US011193085B2

(12) United States Patent
Yamaguchi et al.

(10) Patent No.: US 11,193,085 B2
(45) Date of Patent: Dec. 7, 2021

(54) FREE-POLYUNSATURATED-FATTY-ACID-CONTAINING COMPOSITION AND METHOD FOR MANUFACTURING SAME

(71) Applicant: NIPPON SUISAN KAISHA, LTD., Tokyo (JP)

(72) Inventors: Hideaki Yamaguchi, Tokyo (JP); Nobushige Doisaki, Tsukuba (JP); Seizo Sato, Tokyo (JP); Yuhei Kosuge, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 0 days.

(21) Appl. No.: 15/906,645

(22) Filed: Feb. 27, 2018

(65) Prior Publication Data

US 2018/0187126 A1 Jul. 5, 2018

Related U.S. Application Data

(63) Continuation of application No. PCT/JP2016/075445, filed on Aug. 31, 2016.

(30) Foreign Application Priority Data

Aug. 31, 2015 (JP) .............................. JP2015-170856

(51) Int. Cl.
*C11C 3/00* (2006.01)
*A23D 9/007* (2006.01)
*C07C 69/58* (2006.01)
*C07C 57/12* (2006.01)
*A61K 31/201* (2006.01)
*A61K 31/202* (2006.01)
*A23L 33/12* (2016.01)

(52) U.S. Cl.
CPC ................ *C11C 3/00* (2013.01); *A23D 9/007* (2013.01); *A23L 33/12* (2016.08); *A61K 31/201* (2013.01); *A61K 31/202* (2013.01); *C07C 57/12* (2013.01); *C07C 69/58* (2013.01); *A23V 2002/00* (2013.01)

(58) Field of Classification Search
CPC .......... C11C 3/00; C07C 69/58; C07C 57/12; A61K 31/201; A61K 31/202; A23L 33/12; A23D 9/007; A23V 2002/00
See application file for complete search history.

(56) References Cited

U.S. PATENT DOCUMENTS

| 4,615,839 | A  | 10/1986 | Seto et al. |
| 4,874,629 | A  | 10/1989 | Chang et al. |
| 5,719,302 | A  | 2/1998 | Perrut et al. |
| 5,777,141 | A  | 7/1998 | Brunner et al. |
| 8,535,397 | B2 | 9/2013 | D'Addario et al. |
| 8,957,231 | B2 | 2/2015 | Sepulveda Reyes et al. |
| 9,062,275 | B2 | 6/2015 | Cela Lopez |
| 2004/0236128 | A1 | 11/2004 | Rubin |
| 2013/0150602 | A1 | 6/2013 | Kelliher et al. |
| 2014/0005425 | A1 | 1/2014 | Harting Glade et al. |
| 2015/0126760 | A1 | 5/2015 | Doisaki et al. |
| 2016/0317592 | A1 | 11/2016 | Yamaguchi et al. |
| 2017/0000116 | A1 | 1/2017 | Sato et al. |
| 2018/0195021 | A1 | 7/2018 | Kosuge et al. |

FOREIGN PATENT DOCUMENTS

| CA | 2822314 A1 | 7/2012 |
| JP | S60-133094 A | 7/1985 |
| JP | H07-242895 A | 9/1995 |
| JP | H09-238693 A | 9/1997 |
| JP | H10-139718 A | 5/1998 |
| JP | 2002-069475 A | 3/2002 |
| JP | 2004-89048 A | 3/2004 |
| JP | 2007-89522 A | 4/2007 |
| WO | WO-2009/020406 A1 | 2/2009 |
| WO | WO-2013/172346 A1 | 11/2013 |
| WO | WO-2015/083806 A1 | 6/2015 |

(Continued)

OTHER PUBLICATIONS

"P-Anisidine Value", 2.5.3 of the Standard Methods for the Analysis of Fats, Oils, and Related Materials, 2013 Edition, established by Japan Oil Chemists' Society (JOCS), 3 pages.
"Conjugated Unsaturated Fatty Acids (Spectrum Method)", Reference 1.14 of the Standard Methods for the Analysis of Fats, Oils, and Related Materials, 2013 Edition, established by Japan Oil Chemists' Society (JOCS), 2 pages.
English Translation of the Written Opinion dated Nov. 15, 2016 for PCT/JP2016/075445.
English Translation of International Preliminary Report on Patentability dated Mar. 6, 2018 for PCT/JP2016/075445.
JP 2007-089522, Tsunoda Motoo, et al., Method for producing fatty acid composition containing specific highly unsaturated fatty acid in concentrated state, 2007, English translation, 20 pages (Year: 2007).

(Continued)

*Primary Examiner* — Sahar Javanmard
(74) *Attorney, Agent, or Firm* — Faegre Drinker Biddle & Reath LLP

(57) ABSTRACT

Provided is a free-polyunsaturated-fatty-acid-containing composition that has a total metal content of 0.1 ppm or less and that comprises at least one free polyunsaturated fatty acid having 20 or more carbon atoms, in an amount that is at least 80.0% of the amount of fatty acids in the composition; and a method for manufacturing a free-polyunsaturated-fatty-acid-containing composition, comprising: providing a raw material composition containing at least one polyunsaturated fatty acid having 20 or more carbon atoms; performing a hydrolysis treatment on a reaction solution prepared by combining the provided raw material composition, a lower alcohol, water having a total metal content of 0.01 ppm or less, and an alkali catalyst; and limiting the contact between the reaction composition and the metal after the hydrolysis treatment so that the product T [$cm^2 \times days$] of the contact surface area [$cm^2$] per 1 g and the contact time [days] between the composition and the metal is 100 or less.

5 Claims, 1 Drawing Sheet

(56) References Cited

FOREIGN PATENT DOCUMENTS

| WO | WO-2015/083843 A2 | 6/2015 |
| WO | WO-2015/095688 A1 | 6/2015 |

OTHER PUBLICATIONS

Nagao, T., et al., Enzymatic purification of dihomo-gamma-linolenic acid from Mortierella single-cell oil, 2007, Journal of Molecular Catalysis B: Enzymatic, vol. 44, pp. 14-19 (Year: 2007).
"Fatty Acid Composition by GLC," Marine Oils, American Oil Chemists' Society (AOCS) Official Method Ce 1b-89, 5 pages.
International Search Report for PCT/JP2016/075444, dated Nov. 8, 2016.
International Search Report and Written Opinion for PCT/JP2016/075444, dated Nov. 8, 2016 [Japanese language].
English Translation of the Written Opinion for PCT/JP2016/075444, dated Nov. 8, 2016.
"Color (Gardner Method)," 3.2.1.1 of the Standard Methods for the Analysis of Fats, Oils, and Related Materials, 2013 Edition, established by Japan Oil Chemists' Society (JOGS), 1 page.
English Translation of International Preliminary Report on Patentability for PCT/JP2016/075444, dated Mar. 6, 2018.
Yamamura, Ryuji et al., "High Purification of Polyunsaturated Fatty Acids", Journal of Japan Oil Chemists' Society, 1998, vol. 47, No. 5, pp. 449-456, particularly, p. 450 (w/ English translation).
"Basic Oil Analytical Test Methods", 2013 Edition,2.4.2.1-2013 Fatty Acid Composition (FID Isothermal Gas Chromatography) established by the Japan Oil Chemists' Society (JOCS), pp. 1-4 (w/ English translation).
"Basic Oil Analytical Test Methods", 2013 Edition, 2.4.2.2-2013 Fatty Acid Composition (FID Temperature Programmed Gas Chromatography) established by the Japan Oil Chemists' Society (JOCS), pp. 1-4 (w/ English translation).
International Search Report dated Nov. 15, 2016 for PCT/JP2016/075445.
International Search Report and Written Opinion dated Nov. 15, 2016 for PCT/JP2016/075445 [Japanese language].
Extended European search report dated Mar. 15, 2019 for EP 16841891.1.
Canadian Office Action dated Mar. 11, 2019 issued in Canadian patent application No. 2,997,052.
Extended European search report dated Apr. 3, 2019 for EP 16841890.3.
Stamenković et al., "Kinetics of sunflower oil methanolysis at low temperatures", Bioresource Technology, Elsevier, Amsterdam, NL, vol. 99, No. 5, Dec. 15, 2007, pp. 1131-1140.
Database CA Accession No. 195455107.
Miklos, R., et al., "Water and Fat Mobility in Myofibrillar Protein gels Explored by Low-Field NMR", Food Biophysics, vol. 10, No. 3, Mar. 11, 2015, pp. 316-323.
Frankel, Methods to Determine Extent of Oxidation, in Lipid Oxidation (Oily Press Lipid Library Series), The Oily Press Ltd., Dundee, Scotland, 1998, pp. 83-84.
Ma Li, et al., "Food Chemistry and Nutriology," China Light Industry Press Sep. 2007, pp. 127-128.
Uemura, Yoshimitsu et al., "Effect of Temperature on Corrosion Behavior of Metals in Rubber Seed Oil," Journal of the Japan Institute of Energy, 2013, vol. 92, pp. 925-929.
Examination report No. 2 dated Jul. 23, 2019 issued in Australian patent application No. 2016317523.
Chinese Office Action dated Jun. 25, 2021 issued in Chinese patent application No. 201680050276.8 (with English-language machine translation).
Wang, Dongfeng, "Food Chemistry" Chemical Industry Press, p. 91, the $1^{st}$ Version, the $1^{st}$ Impression published in Aug. 2007.

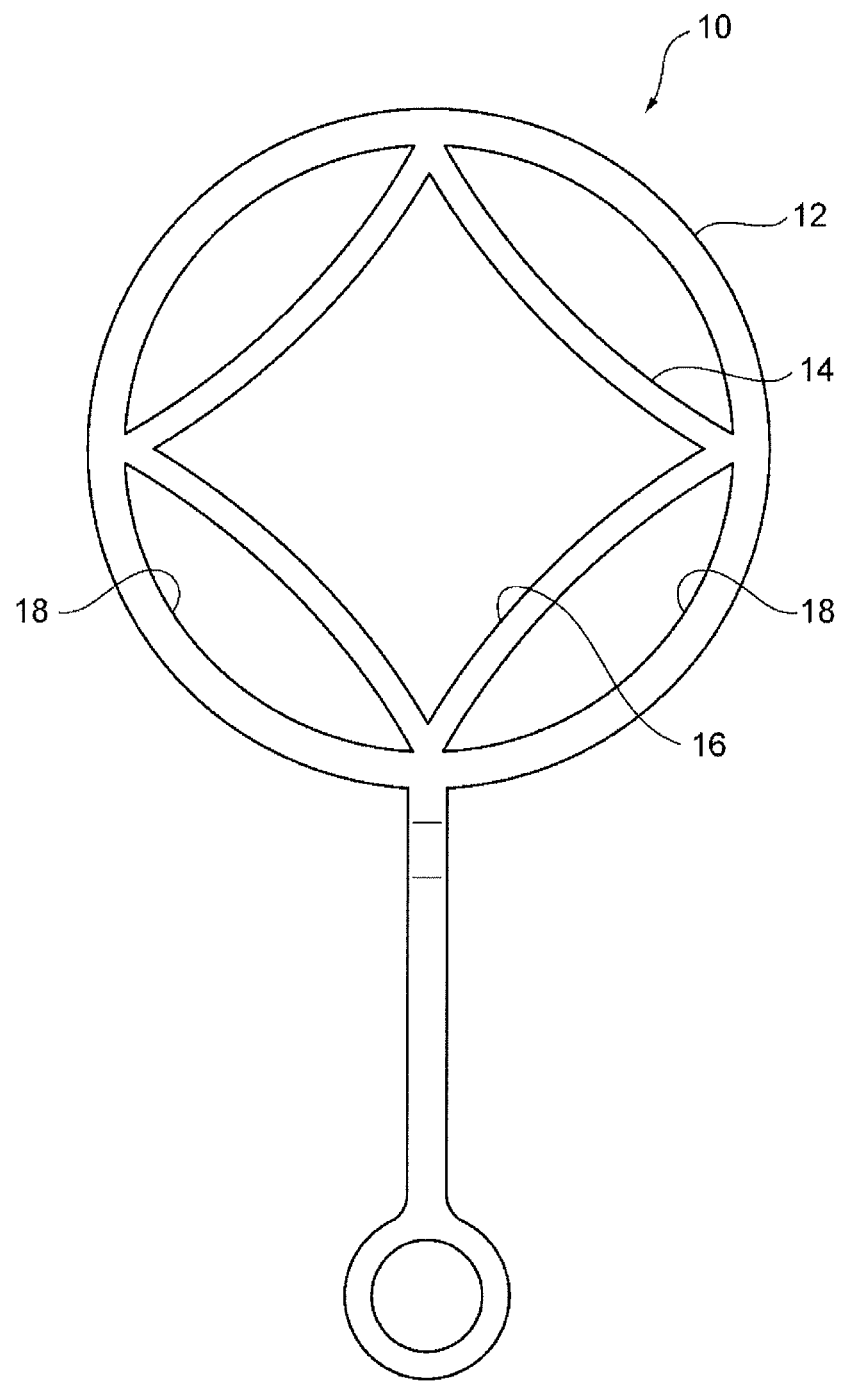

FREE-POLYUNSATURATED-FATTY-ACID-CONTAINING COMPOSITION AND METHOD FOR MANUFACTURING SAME

CROSS REFERENCE TO RELATED APPLICATIONS

This is a continuation application of International Patent Application No. PCT/JP2016/075445 filed Aug. 31, 2016, which claims the benefit of Japanese Patent Application No. 2015-170856, the full contents of all of which are hereby incorporated by reference in their entirety.

BACKGROUND

Technical Field

The present disclosure relates to a free polyunsaturated fatty acid-containing composition and a manufacturing method therefor.

Description of the Related Art

Long-chain polyunsaturated fatty acids having 20 or more carbons, such as eicosadienoic acid, dihomo-γ-linolenic acid (DGLA), eicosatetraenoic acid, arachidonic acid (ARA), eicosapentaenoic acid (EPA), docosatetraenoic acid, docosapentaenoic acid, and docosahexaenoic acid (DHA), have been known to exhibit various functionalities in organisms. Therefore, use of polyunsaturated fatty acids as functional components in products such as medicaments, health food, and cosmetics has been studied. Accordingly, there has been a demand for the production of polyunsaturated fatty acids in large quantities at high concentrations.

In many cases in natural, polyunsaturated fatty acids are present in oils as constituent fatty acids of triacylglycerol (triglyceride). Therefore, to obtain a free polyunsaturated fatty acid, hydrolysis of a constituent fatty acid in triacylglycerol or a fatty acid alkyl ester is typically performed.

For example, WO 2013/172346 discloses that a (free) polyunsaturated fatty acid is obtained by hydrolyzing an ester of polyunsaturated fatty acid obtained by a combination of rectification and column chromatography.

WO 2015/083843 discloses that a free fatty acid of DGLA is obtained by hydrolyzing a DGLA lower alkyl ester, which is obtained by producing a lower alkyl ester of a microbial oil and then rectifying using an alkali catalyst to increase purity.

SUMMARY

To sufficiently exhibit functions of a free polyunsaturated fatty acid, a composition containing high concentration of the free polyunsaturated fatty acid has been desired, and a concentration of a free polyunsaturated fatty acid has been increased by concentration treatment or the like. Meanwhile, even in a case where the same polyunsaturated fatty acid is used as a constituent component, a free fatty acid may have physical or chemical properties that are different from an oil and fat containing a glyceryl ester, such as triacylglycerol, as a main component. Among free fatty acids, physical or chemical properties may significantly vary depending on the structure, such as the length of a chain and the number of double bonds.

As a result, a highly concentrated free polyunsaturated fatty acid may exhibit unexpected behavior when reacted with another component in the composition. Therefore, handling of such a free polyunsaturated fatty acid-containing composition may become complicated when the free polyunsaturated fatty acid-containing composition is used as an added component in a composition containing other various components, such as cosmetic compositions or functional food compositions.

Therefore, demands exist for a free polyunsaturated fatty acid-containing composition by which excellent handling is made possible when the free polyunsaturated fatty acid-containing composition is used as an added component, and a manufacturing method therefor.

Aspects according to the present disclosure include the following.

(1) A free polyunsaturated fatty acid-containing composition, containing at least one free polyunsaturated fatty acid having 20 or more carbons in an amount that a content thereof is 80.0% or greater of fatty acids in the composition and a content of metal being 0.1 ppm or less.

(2) The free polyunsaturated fatty acid-containing composition according to 1, where a peroxide value is 5.0 meq/kg or less.

(3) The free polyunsaturated fatty acid-containing composition according to (1) or (2), where a content of the conjugated unsaturated fatty acid is 1.2% or less of the fatty acids in the composition.

(4) The free polyunsaturated fatty acid-containing composition according to any one of (1) to (3), where an anisidine value is 5.0 or less.

(5) The free polyunsaturated fatty acid-containing composition according to any one of (1) to (4), where the content of the conjugated unsaturated fatty acid is from 0.001% to 1.2% of the fatty acids in the composition.

(6) The free polyunsaturated fatty acid-containing composition according to any one of (1) to (5), where the polyunsaturated fatty acid is at least one selected from the group consisting of eicosadienoic acid, dihomo-γ-linolenic acid, Mead acid, eicosatetraenoic acid, arachidonic acid, eicosapentaenoic acid, docosatetraenoic acid, docosapentaenoic acid, and docosahexaenoic acid.

(7) The free polyunsaturated fatty acid-containing composition according to any one of (1) to (6), where, in a case where membrane evaluation test described below is performed by using the free polyunsaturated fatty acid-containing composition, a time passed until a membrane formed by using a test solution prepared from the free polyunsaturated fatty acid-containing composition is broken is 1.4 or greater with a time (second) passed until a membrane formed by using a reference solution is broken being expressed as 1;
Membrane evaluation test:
a circular frame for test, the circular frame having a plurality of inner frames, is immersed in a fatty acid test solution (a reference solution or a test solution) in a condition at a temperature of 25° C., 1 atmosphere, and a relative humidity of 55%, then membranes are formed in sections formed by the plurality of inner frames by bringing the circular frame above a liquid surface, and a time (second) required for at least one formed membrane to be broken is measured;
Preparation of Test Solution:
Reference Solution:
an aqueous solution of iron (II) sulfate heptahydrate is added to the free polyunsaturated fatty acid composition such that an iron concentration is 100 ppm, ethanol is added and homogenized, and then a solvent is removed by using vacuum to prepare a free polyunsaturated fatty acid composition containing 100 ppm of iron in the composition; and
0.5 g of the free polyunsaturated fatty acid-containing composition containing 100 ppm of iron, 0.15 g of 48 wt. % sodium hydroxide, and 9.35 g of purified water are mixed to prepare an aqueous solution containing approximately 5 wt. % of free polyunsaturated fatty acid sodium in the aqueous solution, and the obtained aqueous solution is used as a reference solution;

Test Solution:

an aqueous solution containing approximately 5 wt. % of free polyunsaturated fatty acid sodium in the aqueous solution is prepared by mixing 0.5 g of the free polyunsaturated fatty acid-containing composition, 0.15 g of 48 wt. % sodium hydroxide, and 9.35 g of purified water, and the obtained aqueous solution is used as a test solution; and Preparation of Circular Frame for Test:

a tool that is formed from plastic and that has five sections divided by inner frames having a thickness of 2 mm in an outer frame having a diameter of 64 mm, an inner diameter of 52 mm, and a thickness of 3 mm is used as the circular frame for test.

(8) The free polyunsaturated fatty acid-containing composition according to any one of (1) to (7), where the metal is iron.

(9) A manufacturing method of a free polyunsaturated fatty acid-containing composition, the method including:

providing a raw material composition containing at least one polyunsaturated fatty acid having 20 or more carbons;

performing hydrolysis treatment on a reaction solution prepared by combining the provided raw material composition, a lower alcohol, water having a total content of metal of 0.01 ppm or less, and an alkali catalyst; and limiting contact between the reaction composition after the hydrolysis treatment and the metal so that a product T ($cm^2 \times day$) of a contact surface area ($cm^2$) per 1 g of the composition and the metal and contact time (day) becomes 100 or less.

(10) The manufacturing method according to (9), where the product T ($cm^2 \times day$) of the contact surface area ($cm^2$) per 1 g of the composition and the metal and the contact time (day) becomes 80 or less.

(11) The manufacturing method according to (9) or (10), where a content of the free polyunsaturated fatty acid having 20 or more carbons in the raw material composition is 80.0% or greater of the fatty acids in the composition.

(12) The manufacturing method according to any one of (9) to (11), where the hydrolysis treatment is performed at a temperature condition of 10° C. or lower.

(13) The manufacturing method according to any one of (9) to (12), where an iron content in the water used for the hydrolysis treatment is 0.01 ppm or less.

(14) The manufacturing method according to any one of (9) to (13), where the polyunsaturated fatty acid in the raw material composition is a polyunsaturated fatty acid alkyl ester.

(15) The manufacturing method according to any one of (9) to (14), where the raw material composition is derived from a microbial raw material.

(16) A storing method of a free polyunsaturated fatty acid-containing composition, the method including: retaining a free polyunsaturated fatty acid-containing composition containing at least one free polyunsaturated fatty acid having 20 or more carbons in an amount that a content thereof is 80.0% or greater of fatty acids in the composition in a condition that limits contact with metal so that a product T ($cm^2 \times day$) of a contact surface area ($cm^2$) per 1 g of the composition and the metal and contact time (day) becomes 100 or less.

(17) The free polyunsaturated fatty acid-containing composition according any one of (1) to (8), where a content of the fatty acid alkyl ester is 0.2% or less of the fatty acids in the composition.

(18) The free polyunsaturated fatty acid-containing composition according to any one of (1) to (8) and (17), where a total content of residual organic solvent in the composition is 5000 ppm or less.

(19) The free polyunsaturated fatty acid-containing composition according to any one of (1) to (8), (17), and (18), where a content of a di- or higher-valent polyunsaturated fatty acid having 18 carbons in the composition is 2.0% or less of the fatty acids in the composition.

(20) A food product, supplement, medicament, cosmetic, or animal feed containing the unsaturated fatty acid-containing composition described in any one of (1) to (8) and (17) to (19).

(21) Use of the unsaturated fatty acid-containing composition described in any one of (1) to (8) and (17) to (19) in a manufacturing method of the food product, supplement, medicament, cosmetic, or animal feed.

According to aspects of the present disclosure, a free polyunsaturated fatty acid-containing composition by which excellent handling as an added component is made possible, and a manufacturing method therefor can be provided.

BRIEF DESCRIPTION OF DRAWINGS

FIG. 1 is a plan view illustrating an example of a circular frame for test that can be used in membrane formation test.

DETAILED DESCRIPTION

The free polyunsaturated fatty acid-containing composition according to an aspect of the present disclosure is a free polyunsaturated fatty acid-containing composition including at least one free polyunsaturated fatty acid having 20 or more carbons in an amount that the content thereof is 80.0% or greater of fatty acids in the composition and the total content of metal being 0.1 ppm or less.

The manufacturing method of the free polyunsaturated fatty acid-containing composition according to an aspect of the present disclosure is a manufacturing method of a free polyunsaturated fatty acid-containing composition, the method including: providing a raw material composition containing at least one polyunsaturated fatty acid having 20 or more carbons; performing hydrolysis treatment on a reaction solution prepared by combining the provided raw material composition, a lower alcohol, water having a total content of metal of 0.01 ppm or less, and an alkali catalyst; and limiting contact between the reaction composition after the hydrolysis treatment and the metal so that the product T ($cm^2 \times day$) of a contact surface area ($cm^2$) per 1 g of the composition and the metal and contact time (day) becomes 100 or less.

A composition containing a free long-chain polyunsaturated fatty acid having 20 or more carbons has higher polarity compared to the polarity of a long-chain polyunsaturated fatty acid in an alkyl ester form or glyceride form and may exhibit different behavior from the behavior of the alkyl ester form or the glyceride form. In particular, in a composition containing free long-chain polyunsaturated fatty acid having 20 or more carbons in an amount that the content thereof is 80.0% or greater of fatty acids in the composition, variation in physical properties may occur although such variation is not observed in a composition containing a similar content of a saturated fatty acid having 18 or less carbons and/or a free unsaturated fatty acid. The inventors of the present disclosure found that a certain relationship exists between such variation of physical properties and the total content of metal.

To further describe this, the following is supposed. It was found that a composition containing a high concentration of free long-chain polyunsaturated fatty acid can elute a greater amount of metal compared to the case of fatty acid having 18 carbons or less. Furthermore, in a highly concentrated free polyunsaturated fatty acid-containing composition, it was found that physical properties or chemical properties of the composition vary when at least a certain content of metal is present.

Based on these findings, according to an embodiment, a highly concentrated free long-chain polyunsaturated fatty acid-containing composition having at most a specific total content of a metal can suppress effect, caused due to the metal in the composition, on variation in physical properties and can provide a composition having excellent stability.

In the free polyunsaturated fatty acid-containing composition according to an embodiment, because the total content of the metal is 0.1 ppm or less, the composition containing a high concentration of the free long-chain polyunsaturated fatty acid can exhibit stable physical properties. As a result, even in the case where a product is formed by combining the free polyunsaturated fatty acid-containing composition according to an embodiment, as a component, with various components.

In the manufacturing method of the free polyunsaturated fatty acid-containing composition according to an embodiment, because the contact between the reaction product after the hydrolysis treatment and the metal is limited so that a product T ($cm^2 \times day$) of a contact surface area ($cm^2$) per 1 g of the composition and the metal and contact time (day) becomes 100 or less, a composition containing a highly concentrated free polyunsaturated fatty acid having 20 or more carbons that has small total content of metal and that has stable physical properties can be efficiently obtained. Note that, in the present specification, the product T ($cm^2 \times day$) of the contact surface area ($cm^2$) per 1 g of the composition and the metal and the contact time (day) may be simply referred to as "product T".

In the storing method of the free polyunsaturated fatty acid-containing composition according to an embodiment, because the composition containing a high concentration of free long-chain polyunsaturated fatty acid is retained in a condition that limits contact with metal so that the product T ($cm^2 \times day$) of the contact surface area ($cm^2$) per 1 g of the composition and the metal and the contact time (day) becomes 100 or less, the highly concentrated free polyunsaturated fatty acid-containing composition during the storage can be maintained in a state that the composition achieves stable physical properties.

The terms "oil" and "oil and fat" in the present specification include oils containing only triglycerides, and also include crude oils containing triglycerides as a main component and other lipids such as diglycerides, monoglycerides, phospholipids, cholesterol, and free fatty acids. "Oil" and "oil and fat" mean compositions containing these lipids.

The term "fatty acid" not only indicates a free saturated or unsaturated fatty acid itself, but also includes fatty acids contained as constituent units in free saturated or unsaturated fatty acids, saturated or unsaturated fatty acid alkyl esters, triglycerides, diglycerides, monoglycerides, phospholipids, steryl esters, and the like, which can also be called constituent fatty acids. In the present specification, unless otherwise noted or indicated, when a fatty acid that is present or used is mentioned, presence or use of fatty acid-containing compounds in any form is included. Examples of forms of compounds containing fatty acids include a free fatty acid form, a fatty acid alkyl ester form, a glyceryl ester form, a phospholipid form, and a steryl ester form. When a fatty acid is specified, one form may be present, or a mixture of two or more forms may be present.

It has been empirically determined that the reaction efficiency of hydrolysis of fatty acids is high, and after hydrolysis, a composition containing mainly fatty acid in a form of free fatty acids is obtained. For this reason, unless otherwise specified, fatty acids after the processing step may be denoted while omitting that they are a composition or that the fatty acid is of a free fatty acid form. However, this does not completely negate the fact that fatty acids in a form other than a free fatty acid form are included.

It has been empirically determined that the reaction efficiency of alcoholysis of oils and fats or fatty acid esters is high, and after alcoholysis, a composition containing mainly fatty acid in a fatty acid alkyl ester form is obtained. For this reason, unless otherwise specified, fatty acids after the processing step are denoted while omitting that they are a composition or that the fatty acid is in an alkyl ester form. However, this does not completely negate the fact that fatty acids in a form other than an alkyl ester form are included.

When denoting fatty acids, a numerical expression may be used, whereby the number of carbons, the number of double bonds, and the locations of double bonds are each expressed in a simplified manner using numbers and alphabets, respectively. For example, a saturated fatty acid having 20 carbons is denoted as "C20:0". A monounsaturated fatty acid having 18 carbons is denoted as "C18:1" or the like. Dihomo-γ-linolenic acid is denoted as "C20:3, n-6" or the like. Note that "n-6" is denoted also as ω-6, and this indicates that the bonding position of a first double bond is at the sixth position when the position is counted from the last carbon (ω) to the carboxy group. This method is known to those of ordinary skill in the art, and those of ordinary skill in the art can easily specify fatty acids expressed in accordance with this method.

In the present specification, the term "crude oil" means a mixture of the lipids described above, and means an oil in the state obtained by extraction from an organism. In the present specification, the term "refined oil" means an oil from which substances, such as phospholipids and cholesterol, other than the target substance which have been removed by performing at least one oil and fat refining process selected from the group consisting of a degumming process, a deacidification process, a decoloring process, and a deodorizing process.

In the present specification, in addition to an independent step, the term "step" also refers to a step that achieves an intended object of the step even when the step cannot be clearly distinguished from other steps.

In the present specification, numeric ranges indicated by "to" are ranges that include the minimum and maximum values each stated before and after the "to." In the present specification, the terms "not greater than" and "less than" in regard to percentages mean ranges including 0%, which is the case of "not contained", or a value undetectable by present means, unless the lower limit is specifically stated.

In the present specification, in a case where multiple substances corresponding to each of the components in the composition are present, the amount of each component in the composition, unless otherwise noted, is taken to mean the total amount of these multiple substances present in the composition. In the present specification, in the case where multiple substances corresponding to each of the components in the composition are present, the content of each component in the composition, unless otherwise noted, is taken to mean the total content of these multiple substances present in the composition.

In the present specification, unless otherwise noted, when a numerical range that only specifies one or a plurality of upper limit values and a numerical range that only specifies one or a plurality of lower limit values are described for an identical target, an embodiment of the present disclosure includes a numerical range having a combination of any upper limit value that is chosen from the one or the plurality of the upper limit values and any lower limit value that is chosen from the one or the plurality of the lower limit values.

The content of the fatty acids in the composition of the present specification is determined based on the fatty acid composition unless otherwise noted. The composition of fatty acids may be determined by a normal method. Specifically, when the fatty acids in the composition to be measured are substances other than fatty acid lower alkyl esters, fatty acid lower alkyl esters, which is obtained by subjecting the fatty acids to be measured to esterification by using a lower alcohol and a catalyst, are used. When the fatty acids in the composition to be measured are fatty acid lower alkyl esters, the fatty acids to be measured are used as is. Thereafter, the obtained fatty acid lower alkyl esters are analyzed as a sample using gas chromatography. Peaks corresponding to each of the fatty acids are identified in the obtained gas chromatography chart, and the peak area of each of the fatty acids is determined using the Agilent ChemStation integration algorithm (revision C.01.03[37], Agilent Technologies). "Peak area" indicates a ratio (area percent) of the peak area for respective components to the area of all peaks as determined in charts analyzed by gas chromatography, thin-layer chromatography/flame ionization detector (TLC/FID) or the like of oil and fat having various fatty acids as constituent components, and indicates the content ratio of the component of the peak. The value according to the area percent obtained by the measurement method described above is the same as the value according to the weight percent of each fatty acid relative to the total weight of the fatty acids in a sample, and may be used interchangeably. Refer to "Basic Oil Analytical Test Methods", 2013 Edition, 2.4.2.1-2013 Fatty Acid Composition (FID constant temperature gas chromatograph method) and 2.4.2.2-2013 Fatty Acid Composition (FID heating gas chromatograph method) established by the Japan Oil Chemists' Society (JOCS).

The fatty acid composition was determined by gas chromatography by the method indicated in the examples. Detailed conditions are indicated in examples.

Free Polyunsaturated Fatty Acid-Containing Composition

The free polyunsaturated fatty acid-containing composition in an embodiment is a free polyunsaturated fatty acid-containing composition containing at least one free polyunsaturated fatty acid having 20 or more carbons in an amount that a content thereof is 80.0% or greater of fatty acids in the composition, and the total content of metal is 0.1 ppm or less.

In the free polyunsaturated fatty acid-containing composition according to the present embodiment, because the total content of the metal is 0.1 ppm which is low, the physical properties of the composition containing the free polyunsaturated fatty acid having 20 or more carbons in an amount that the content thereof is 80.0% or greater of the fatty acids can be stabilized, and excellent handling is made possible even when the free polyunsaturated fatty acid-containing composition is used as an added component to other compositions.

In the present specification, unless otherwise noted, the free polyunsaturated fatty acid having 20 or more carbons may be referred to as "free LC-PUFA". In the present specification, the free polyunsaturated fatty acid-containing composition according to an embodiment of the present disclosure may be simply referred to as "free LC-PUFA-containing composition".

In the present specification, examples of the stable physical properties exhibited by the free LC-PUFA-containing composition include effect on temperature of crystal formation, stability of membrane, foam, and surface tension, and stability against acidification.

The temperature of crystal formation of the composition may be determined by any measurement method that is publicly known in the art, and examples of the method include a method of measuring a temperature at which the composition undergoes phase transition from the solid phase to the liquid phase, a method of measuring a temperature at which the composition undergoes phase transition from the liquid phase to the solid phase, and the like. When the temperature of crystal formation of the composition is increased by at least 1° C. compared to the solidification temperature of a free LC-PUFA-containing composition having a total content of metal of 0 ppm, it can be determined that the viscosity of the composition may change. The free LC-PUFA-containing composition according to an embodiment can exhibit an increase in the solidification temperature by lower than +1° C., or by lower than +0.5° C., compared to the solidification temperature of the free LC-PUFA-containing composition having a total content of metal of 0 ppm.

The stability of the membrane of the composition can be determined by forming a thin membrane by using soapy water for measurement (alkali aqueous solution of fatty acid) prepared by using the free LC-PUFA-containing composition and then measuring the retention time of the formed thin membrane. Specifically, the following evaluation method is applicable.

Membrane Evaluation Test

A circular frame for test, the circular frame having a plurality of inner frames, is immersed in a fatty acid test solution (a reference solution or a test solution) in a condition at a temperature of 25° C., 1 atmosphere, and a relative humidity of 55%, then membranes are formed in sections (spaces) formed by the plurality of inner frames by gradually bringing the circular frame above a liquid surface, and a time (second) required for at least one formed membrane to be broken is measured. As the fatty acid test solution used herein, a reference solution or a test solution described below is used. As the circular frame for test used for the measurement, a circular frame for test described below is used.

Preparation of Test Solution

Reference Solution

An aqueous solution of iron(II) sulfate heptahydrate is added to the free polyunsaturated fatty acid composition to allow an iron concentration to be 100 ppm, ethanol is added and homogenized, and then a solvent is removed by vacuum drawing to prepare a free polyunsaturated fatty acid composition containing 100 ppm of iron in the composition. 0.5 g of the free polyunsaturated fatty acid-containing composition containing 100 ppm of iron, 0.15 g of 48 wt. % sodium hydroxide, and 9.35 g of purified water are mixed to prepare an aqueous solution containing approximately 5 wt. % of free polyunsaturated fatty acid sodium in the aqueous solution, and the obtained aqueous solution is used as a "reference solution". "Approximately 5 wt. %" in the reference solution refers to a range of 4.5 wt. % to 5.5 wt. %.

Test Solution

An aqueous solution containing approximately 5 wt. % of free polyunsaturated fatty acid sodium in the aqueous solution is prepared by mixing 0.5 g of the free polyunsaturated fatty acid-containing composition, 0.15 g of 48 wt. % sodium hydroxide, and 9.35 g of purified water, and the obtained aqueous solution is used as a "test solution" of the evaluation target. The free polyunsaturated fatty acid-containing composition used for preparing the test solution is a composition from which the solvent is removed by an evaporator or vacuum drawing. "Approximately 5 wt. %" in the test solution refers to a range of 4.5 wt. % to 5.5 wt. %.

Preparation of Circular Frame for Test

A tool that is formed from plastic and that has five sections divided by inner frames having a thickness of 2 mm in an outer frame having a diameter of 64 mm, an inner diameter of 52 mm, and a thickness of 3 mm is prepared as the circular frame for test. The sizes of the sections segmented by the inner frames may be uniform or different. FIG. 1 illustrates a circular frame for test 10 according to an embodiment.

The circular frame for test 10 has an outer frame 12 having a circular shape and a plurality of inner frames 14 that are connected to the outer frame 12. The outer frame 12 has an outer diameter of 64 mm, an inner diameter of 52 mm, and a thickness of 3 mm. In the inner part of the circular outer frame 12, a large section 16 enclosed by the plurality of inner frames 14 and four small sections 18 enclosed by the inner frame 14 and the outer frame 10. The circular frame for test 10 has the total of five sections.

In the case where the membrane evaluation test described above is applied, a relative value of time (retention time (second)) passed until a membrane that has been formed by using a test solution is broken is preferably 1.2 or greater, 1.3 or greater, 1.4 or greater, 1.5 or greater, or 1.6 or greater with a time (retention time (second)) passed until a membrane formed by using a reference solution is broken being expressed as 1. When the relative time is in this range, the free LC-PUFA-containing composition is evaluated as being a free LC-PUFA-containing composition having a sufficiently low content of metal and having stable physical properties. The upper limit value of this relative value is not particularly limited and, for example, may be 3.0 or less.

The polyunsaturated fatty acid having 20 or more carbons in the free LC-PUFA-containing composition includes di- or higher valent unsaturated fatty acids and, preferably, tri- or higher valent unsaturated fatty acids. The number of carbon atoms of the polyunsaturated fatty acid refers to the number of carbon atoms of the constituent fatty acids. Examples of polyunsaturated fatty acid having 20 or more carbons include polyunsaturated fatty acids having from 20 to 22 carbons. Specific examples thereof include eicosadienoic acid (C20:2, n-9, EDA), dihomo-γ-linolenic acid (C20:3, n-6, DGLA), Mead acid (C20:3, n-9, MA), eicosatetraenoic acid (C20:4, n-3, ETA), arachidonic acid (C20:4, n-6, ARA), eicosapentaenoic acid (C20:5, n-3, EPA), docosatetraenoic acid (C22:4, n-6, ETA), docosapentaenoic acid (C22:5, n-3, $_{n-3}$DPA), docosapentaenoic acid (C22:5, n-6, $_{n-6}$DPA), and docosahexaenoic acid (C22:6, 11-3, DHA). The free LC-PUFA-containing composition needs to contain at least one of these polyunsaturated fatty acids and may contain a combination of two or more of these. Examples of the LC-PUFA having a combination of two or more of these include a combination of DGLA and EPA, a combination of DGLA and $_{n-3}$DPA, a combination of DGLA and DHA, a combination of ARA and EPA, a combination of ARA and $_{n-3}$DPA, a combination of ARA and DHA, a combination of EPA and $_{n-3}$DPA, a combination of DHA and $_{n-3}$DPA, a combination of DHA and EPA, and a combination of EPA and DHA and $_{n-3}$DPA.

The free LC-PUFA-containing composition contains one selected from the polyunsaturated fatty acids described above and may contain no other polyunsaturated fatty acids, or does not need to contain other particular one or two or more polyunsaturated fatty acids described above as long as the free LC-PUFA-containing composition contains at least one polyunsaturated fatty acid having from 20 to 22 carbons described above as LC-PUFA. For example, the free LC-PUFA-containing composition may be prepared so as to not contain at least one type selected from the group consisting of eicosadienoic acid (C20:2, n-9), dihomo-γ-linolenic acid (C20:3, n-6), Mead acid (C20:3, n-9), eicosatetraenoic acid (C20:4, n-3), arachidonic acid (C20:4, n-6), eicosapentaenoic acid (C20:5, n-3), docosatetraenoic acid (C22:4, n-6), docosapentaenoic acid (C22:5, n-3), docosapentaenoic acid (C22:5, n-6), and docosahexaenoic acid (C22:6, n-3). Here, "not containing polyunsaturated fatty acids" means that the content of the target polyunsaturated fatty acid is less than 5% or 0% of the fatty acids in the composition.

The content of the LC-PUFA in the free LC-PUFA-containing composition is 80.0% or greater of the fatty acids in the composition. Because the free LC-PUFA-containing composition containing 80.0% or greater of the LC-PUFA can exhibit superior functions of LC-PUFA. The lower limit value of the content of the target LC-PUFA in the free LC-PUFA-containing composition may be 85.0%, 90.0%, 95.0%, 97.0%, 98.0%, 99.0%, or 99.5% of the fatty acids in the composition. When the content of the LC-PUFA is higher, superior functions of the LC-PUFA can be exhibited. The upper limit value of the content of the LC-PUFA is not particularly limited and, for example, the upper limit value may be 99.9% or 98.0%. The content of the LC-PUFA in the present composition may be in a range of any combination of a chosen value of the upper limit value and a chosen value of the lower limit value described above. For example, the content may be from 80.0% to 99.9%, from 90.0% to 99.9%, from 90.0% to 98%, from 95.0% to 99.9%, from 97.0% to 99.9%, or from 97.0% to 98.0% of the fatty acids in the composition.

The total content of the metal in the free LC-PUFA-containing composition is 0.1 ppm or less. Because the total content of the metal in the free LC-PUFA-containing composition is 0.1 ppm or less, variation in the physical properties of the composition due to the free LC-PUFA can be reduced. The content of the iron in the free LC-PUFA-containing composition may be 0.08 ppm or less, 0.05 ppm or less, 0.03 ppm or less, 0.01 ppm or less, or 0.00 ppm.

The free LC-PUFA-containing composition having excellent stability based on the membrane evaluation test described above may have the total content of the metal, representatively the content of iron, of 0.05 ppm or greater or 0.1 ppm or greater, and in this case, the total content of the metal, representatively the content of iron, may be 1.2 ppm or less or 1.0 ppm or less. The free LC-PUFA-containing composition having excellent stability based on the membrane evaluation test described above may have the relative value of the membrane evaluation test described above of 1.8 or greater, 1.9 or greater, 2.0 or greater, or 2.2 or greater. The upper limit value of this relative value is not particularly limited and, for example, may be 3.0 or less.

Examples of the "metal" in the present specification include iron, copper, chromium, aluminum, nickel, tin, zinc, manganese, and molybdenum. A representative example is iron. One type of these metals may be used alone, or two or more types of these metals may be used. In the present specification, when one type of metal is present in the composition, "total content of metal" means the content of the one type of metal present in the composition. When two or more types of metals are present in the composition, "total content of metal" means the total content of these. Because, in many cases, iron can correspond to the metal that may be present in the free LC-PUFA-containing composition, the content of the iron may be used as the "total content of metal".

The iron in the present specification means iron measured by atomic absorption spectrometry (graphite furnace method). In the present specification, the content of the iron is measured in accordance with the molecular absorption spectrometry by using the following conditions.

After 1 g of the target sample is weighed and 0.15 mL of nitric acid (for measuring harmful metals) is added thereto, the mixture is diluted with methyl isobutyl ketone in a volumetric flask to 10 mL total and used as a sample solution.

The reference sample is Conostan S-21 (10 ppm (wt.)). This reference sample is diluted with methyl isobutyl ketone to prepare calibration curve samples (0 μg/L, 10 μg/L, and 20 μg/L).

The sample solution and the reference samples are subjected to atomic absorption spectrometry in appropriate conditions for the used analytical instrument for iron quantitation by the graphite furnace method, for example, in the following analysis conditions. The iron content in the sample solution is quantitated by automatic calculation by the software provided with the instrument.

Instrument: Z-2000, Zeeman Atomic Absorption Spectrophotometer (Hitachi, Ltd.)
Injection amount: 20 μL
Measurement mode: graphite atomizer/autosampler
Measured element: Fe
Cuvette: Pyro tube HR
Measured wavelength (nm): 248.3
Measurement signal: BKG correction
Slit width (nm): 0.2
Time constant (s): 0.1
Lamp current (mA): 12.5
Heat control method: light temperature control
Temperature Program
1 Drying: from 80° C. to 140° C.; time for temperature increase: 40 seconds; retention time: 0 seconds; gas flow rate: 200 mL/min
2 Ashing: at 1000° C.; time for temperature increase: 20 seconds; retention time: 0 seconds; gas flow rate: 200 mL/min
3 Atomization: at 2400° C.; time for temperature increase: 0 seconds; retention time: 5 seconds; gas flow rate: 30 mL/min
4 Cleaning: at 2700° C.; time for temperature increase: 0 seconds; retention time: 4 seconds; gas flow rate: 200 mL/min
5 Cooling: at 0° C.; time for temperature increase: 0 seconds; retention time: 10 seconds; gas flow rate: 200 mL/min Specifically, the iron content in the sample solution is calculated based on the following Equation (I):

$$\text{The iron content in the sample (ppm)} = C/(W \times 100) \quad (I)$$

where C represents the iron content (μg/L) of the sample solution obtained by the atomic absorption spectrometry, and W represents the sampled amount (g) of the sample solution.

The free LC-PUFA-containing composition according to an embodiment can satisfy at least one selected from the following conditions (1) to (3), in addition to the total content of metal described above.

(1) Peroxide Value

In the free LC-PUFA-containing composition according to an embodiment, the peroxide value may be 5.0 meq/kg or less. The free LC-PUFA-containing composition having the peroxide value of 5.0 meq/kg or less can exhibit excellent storage stability. The peroxide value of the free LC-PUFA-containing composition may be 5.0 meq/kg or less, 4.0 meq/kg, 3.5 meq/kg or less, or 3.0 meq/kg or less. The peroxide value is determined in accordance with the ferric thiocyanate method.

(2) Conjugated Unsaturated Fatty Acid

In the free LC-PUFA-containing composition, the content of the conjugated unsaturated fatty acid may be 1.2% or less of the fatty acids in the composition. Although the conjugated unsaturated fatty acid differs depending on the type of the fatty acid and the type of the LC-PUFA in the raw material composition used for the hydrolysis treatment, examples of the conjugated unsaturated fatty acid include conjugated dienoic acid, conjugated trienoic acid, and conjugated tetraenoic acid. The conjugated unsaturated fatty acid can be quantified based on the absorbance of the target conjugated unsaturated fatty acid. The content of the conjugated unsaturated fatty acid in the free LC-PUFA-containing composition is a content of the conjugated unsaturated fatty acid obtained by measuring ultraviolet spectrum of a sample and calculating using a stipulated calculation formula, and is a value measured in accordance with the conjugated unsaturated fatty acid (spectrum method) stipulated in Reference 1.14 of Standard Methods for the Analysis of Fats, Oils, and Related Materials, 2013 Edition, established by Japan Oil Chemists' Society (JOCS). When the composition in the sample contains a component other than the fatty acids, the amount of the conjugated unsaturated fatty acid can be determined based on the amount of the fatty acids in the composition.

The content of the conjugated unsaturated fatty acid in the free LC-PUFA-containing composition may be 1.0% or less, 0.8% or less, 0.7% or less, 0.6% or less, 0.5% or less, 0.4% or less, or 0.3% or less, of the fatty acids in the composition. A smaller content of the conjugated unsaturated fatty acid tends to exhibit superior oxidation stability of the composition. The lower limit value of the content of the conjugated unsaturated fatty acid may be 0.1%, 0.2%, 0.01%, or 0.001%. For example, the content of the conjugated unsaturated fatty acid of the free LC-PUFA-containing composition may be from 0.001% to 1.2%, from 0.001% to 1.0%, from 0.01% to 0.8%, from 0.1% to 0.7%, or from 0.2% to 0.7%, of the fatty acids in the composition.

(3) Anisidine Value

In the free LC-PUFA-containing composition according to an embodiment, the anisidine value (AnV) may be 5.0 or less, 4.5 or less, 4.0 or less, 3.5 or less, 3.0 or less, or 2.5 or less. The anisidine value is an indicator varied based on the content of the oxidized substance present in the free LC-PUFA-containing composition. The free LC-PUFA-containing composition showing a lower anisidine value has a smaller content of the oxidized substance. The anisidine value is determined based on 2.5.3 of the Standard Methods for the Analysis of Fats, Oils, and Related Materials, 2013 Edition, established by Japan Oil Chemists' Society (JOCS).

The free LC-PUFA-containing composition includes the following, for example:

(a) a free LC-PUFA-containing composition having the content of the iron of 0.1 ppm or less, the peroxide value of 5.0 meq/kg or less, and the content of the conjugated unsaturated fatty acid of 1.2% or less of the fatty acids in the composition;

(b) a free LC-PUFA-containing composition having the content of the iron of 0.1 ppm or less, the peroxide value of 4.0 meq/kg or less, and the content of the conjugated unsaturated fatty acid of 1.0% or less of the fatty acids in the composition;

(c) a free LC-PUFA-containing composition having the content of the iron of 0.1 ppm or less, the content of the conjugated unsaturated fatty acid of 1.2% or less of the fatty acids in the composition, and the anisidine value of 3.5 or less;

(d) a free LC-PUFA-containing composition having the content of the iron of 0.1 ppm or less, the peroxide value of 4.5 meq/kg or less, and the anisidine value of 5.0 or less; and (e) a free LC-PUFA-containing composition having the content of the iron of 0.1 ppm or less, the peroxide value of 5.0 meq/kg or less, the content of the conjugated unsaturated fatty acid of 1.2% or less of the fatty acids in the composition, and the anisidine value of 4.0 or less.

In the free LC-PUFA-containing composition of (a), (c), or (d) described above, the peroxide value may be 3.5 meq/kg or less or 2.5 meq/kg. In the free LC-PUFA-containing composition of (a), (b), or (d) described above, the content of the conjugated unsaturated fatty acid may be 0.8% or less, 0.7% or less, 0.6% or less, 0.4% or less, or 0.3% or less. In the free LC-PUFA-containing composition of (b), (c), or (d) described above, the anisidine value may be 4.5 or less, 4.0 or less, 3.5 or less, 3.0 or less, or 2.5 or less.

The free LC-PUFA-containing composition may have a small content of the fatty acid alkyl ester. In the step of producing a free fatty acid, the fatty acid alkyl ester may be a raw material substance of alkaline hydrolysis or may be a product that can be produced from the free fatty acid through a reverse reaction. The free LC-PUFA-containing composition having a smaller content of the fatty acid alkyl ester can have a higher content of the free LC-PUFA and tends to exhibit superior bioabsorbability, especially superior intestinal absorbability, of the composition. The content of the fatty acid alkyl ester of the free LC-PUFA-containing composition may be 0.2% or less, 0.1% or less, 0.05% or less, 0.04% or less, 0.03% or less, 0.02% or less, or 0.01% or less, of the fatty acids in the composition. The lower limit value of the content of the fatty acid alkyl ester is not particularly limited, and for example, the lower limit value may be 0.0005%. When the content of the fatty acid alkyl ester is 0.0005% or greater, the composition is less likely to crystallize, and the flowability tends to be enhanced.

The free LC-PUFA-containing composition may be a free LC-PUFA-containing composition having a smaller content of fatty acids other than the LC-PUFA. When the content of the fatty acids other than the LC-PUFA in the composition is low, exhibition of functions is expected in a degree corresponding to the content of the LC-PUFA, and also effect due to other fatty acids other than the LC-PUFA can be suppressed. Examples of other fatty acids that can reduce the content thereof in the free LC-PUFA-containing composition include saturated or unsaturated fatty acids having less than 20 carbons, and saturated fatty acids having 22 or more carbons. Specific examples of the saturated or unsaturated fatty acid having less than 20 carbons include saturated fatty acids having 18 carbons, monounsaturated fatty acids having 18 carbons, divalent unsaturated fatty acids having 18 carbons, trivalent unsaturated fatty acids having 18 carbons, and tetravalent unsaturated fatty acids having 18 carbons. Examples of the saturated fatty acid having 22 or more carbons include saturated fatty acids having 22 carbons and saturated fatty acids having 24 carbons.

Among these fatty acids other than the LC-PUFA, the free LC-PUFA-containing composition may be a free LC-PUFA-containing composition having a low content of a di- or higher-valent polyunsaturated fatty acid having 18 carbons. For example, the content of the di- or higher-valent polyunsaturated fatty acid having 18 carbons may be 2.0% or less, 1.5% or less, 1.0% or less, or 0.8% or less, of the fatty acids in the composition. The lower limit value of the content of the fatty acids other than the LC-PUFA may be, for example, 0.001% or greater, 0.005% or greater, or 0.01%. The content of the di- or higher-valent polyunsaturated fatty acid having 18 carbons may be, for example, from 0.001% to 2.0%, from 0.005% to 1.5%, from 0.01% to 1.5%, or from 0.01% to 1.0%.

The free LC-PUFA-containing composition may contain a fatty acid in a form other than the fatty acids described above. Examples of the fatty acids in other forms include triglyceride, diglyceride, monoglyceride, phospholipid, and steryl esters. The content of the fatty acids in other forms needs to be an amount that corresponds to the rest of the free LC-PUFA-containing composition excluding the LC-PUFA. The content may be less than 20.0%, less than 10.0%, less than 5.0%, less than 2.0%, less than 1.0%, or less than 0.5%, of the fatty acids in the composition.

The content of the fatty acids in the free LC-PUFA-containing composition may be 97.0 wt. % or greater, 98.0 wt. % or greater, 99.0 wt. % or greater, 99.5 wt. % or greater, or 99.9 wt. % or greater, of the total weight of the composition. The content of the fatty acids in the free LC-PUFA-containing composition can be confirmed by a publicly known technique, such as TLC/FID. The free LC-PUFA-containing composition may contain a component other than the fatty acids. Examples of such other component that may be contained in the free LC-PUFA-containing composition include antioxidants, such as tocopherol, vitamin C, and vitamin C derivatives, and solvents, such as ethanol.

The free LC-PUFA-containing composition may be produced by any manufacturing method as long as the free LC-PUFA-containing composition has characteristics described in the present specification, and preferably is a free LC-PUFA-containing composition produced by the manufacturing method described below.

Manufacturing Method

The manufacturing method of the free LC-PUFA-containing composition according to an embodiment of the present disclosure includes: providing a raw material composition containing at least one polyunsaturated fatty acid having 20 or more carbons; performing hydrolysis treatment of a reaction solution prepared by combining the provided raw material composition, a lower alcohol, water having a total content of metal of 0.01 ppm or less, and an alkali catalyst; and limiting contact between the reaction composition after the hydrolysis treatment and the metal so that a product T ($cm^2 \times day$) of a contact surface area ($cm^2$) per 1 g of the composition and the metal and contact time (day) becomes 100 or less; and, as necessary, another step(s). According to the manufacturing method of the present embodiment, a free LC-PUFA-containing composition having the total content of the metal of, representatively the content of the iron of, 0.1 ppm or less can be efficiently obtained.

In the step of providing the raw material composition, a raw material composition that had been acquired may be provided or a raw material composition that had been separately produced may be provided as long as the raw material composition contains at least one LC-PUFA. The raw material composition may be a raw material composition derived from an organism, such as a raw material composition derived from a marine raw material, a raw material composition derived from a microbial raw material, a raw material composition derived from a plant raw material, and a raw material composition derived from an animal raw material. The raw material composition may be a composition containing LC-PUFA in a triglyceride form, and may be a composition containing an LC-PUFA alkyl ester. The LC-PUFA alkyl ester-containing composition is preferably obtained by subjecting a bio-oil containing LC-PUFA in a triglyceride form to alkyl esterification.

The bio-oil containing LC-PUFA may be a bio-oil, such as a marine raw material oil derived from fish or the like, a microbial oil derived from microorganisms, and a plant oil derived from plants, and for example, may be a microbial oil. The bio-oil means an oil obtained by using biomass as its origin, and the microbial oil means an oil obtained by using microbial biomass as its origin. The bio-oil may be a bio-oil that originates from genetically modified materials. The term "biomass" means an aggregation or lump of cells at a certain point of time during growth in a certain region or in an ecosystem.

Examples of the marine raw material oil include lipids including oils and fats, phospholipids, wax esters, and the like contained in fish, shellfish, or marine animals. Examples of the marine raw material oil include oils derived from fish such as herring, sardine, anchovy, menhaden, pilchard, saury, tuna, bonito, hake, catfish, capelin, red fish, white fish, mackerel, jack mackerel, yellowtail, sand eel, pout, salmon, pollock, cod, halibut, trout, blue whitening, sprat, shark, and dogfish; oils derived from mollusks such as squid, clam, and abalone; oils derived from crustaceans such as krill; oils derived from animals such as seal, sealion, sea bear, and walrus, and mixtures of these oils.

The microorganism may be a microorganism that produces lipids or a microorganism that can produce lipids, and examples thereof include algae, true fungi, bacteria, fungi, and stramenopiles.

Examples of the algae include the genus *Labyrinthula* (*Labyrinthula mycota*).

Examples of the true fungi include the genus *Yarrowia*, the genus *Candida*, the genus *Saccharomyces*, the genus *Schizosaccharomyces*, and the genus *Pichia*.

Examples of the bacteria include *Agrobacterium, Bacillus, Escherichia, Pseudomonas*, and *Actinomyces*.

Examples of the fungi include at least one type selected from the group consisting of the genus *Mortierella*, the genus *Conidiobolus*, the genus *Phythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium*, and the genus *Saprolegnia*. Of these, microorganisms belonging to the genus *Mortierella* are even more preferable. Examples of the microorganisms belonging to the genus *Mortierella* include microorganisms belonging to the subgenus *Mortierella* such as *Mortierella elongata, Mortierella exigua, Mortierella hygrophila*, and *Mortierella alpina*.

Examples of the plant include plants of the genus *Brassica*, the genus *Helianthus*, the genus *Gossypium*, the genus *Linum*, the genus *Nicotiana*, the genus *Citrus*, the genus *Allium*, the genus *Triticum*, the genus *Hordeum*, the genus *Avena*, the genus *Secale*, the genus *Oryza*, the genus *Saccharum*, the genus *Zea*, the genus *Sorghum* as well as soybean, tomato, potato, pea, frijol, peanut, Medicago, celery, paseley, clover, carrot, radish, sugar beet, cucumber, spinach, cassava, olive, apple, banana, melon, grape, strawberry, coconut plant, coffee plant, and pepper.

The raw material oil that is subjected to the alkyl esterification may be a crude oil or a refined oil. The crude oil may be an oil obtained from a marine raw material or may be an oil obtained from a microbial raw material. A refined oil can be obtained by subjecting a crude oil to a de-gumming process, deacidification process, decoloration process using an activated clay or active carbon, washing process, deodorization process by steam distillation or the like, and crude oil refining process that removes substances other than the target, such as phospholipids and sterols.

In the step of performing alkyl esterification, the raw material oil is decomposed into a lower alkyl ester via alcoholysis using a lower alcohol. Examples of the lower alcohol include lower alcohols typically used in alkyl esterification of fatty acids, such as lower alcohols having from 1 to 3 carbons. In the alcoholysis, a lower alcohol such as ethanol and a catalyst or enzyme are added and reacted with a raw material oil to produce an ethyl ester from the fatty acid bonded to glycerin. As the catalyst, an alkali catalyst, an acid catalyst, or the like is used. As the enzyme, lipase is used.

The crude oil or the refined oil, or the fatty acid alkyl ester-containing composition obtained by the alkyl esterification treatment may contain at least one other fatty acid in addition to the target LC-PUFA. One type of method or a combination of two or more types of methods, exemplified by the distillation, rectification, column chromatography, low temperature crystallization method, urea clathrate method, liquid-liquid countercurrent distribution chromatography, or the like, may be used to concentrate or isolate the particular LC-PUFA from the crude oil, the refined oil, or the fatty acid alkyl ester-containing composition. A combination of distillation or rectification, and column chromatography or liquid-liquid countercurrent distribution chromatography is preferably used. When the step of concentrating or isolating the particular LC-PUFA is performed, the content of target LC-PUFA, which may be contained in the final LC-PUFA-containing composition, in the fatty acids is increased and the content of other fatty acid other than the target LC-PUFA in the fatty acids can be reduced.

For example, in a case in which rectification is used, the rectification step is preferably carried out by distillation using a reduced pressure at the top of the distillation column of less than or equal to 10 mmHg (1333 Pa), using a temperature of the column bottom in the range of 165° C. to 210° C., and preferably 170° C. to 195° C., from the perspective of suppressing the denaturation of the fatty acid due to heat, and increasing efficiency of rectification. The pressure at the top of the distillation column is preferably as low as possible, and more preferably lower than or equal to 0.1 mmHg (13.33 Pa). No particular limitation is imposed on the temperature at the top of the column, and for example, this temperature may be set to lower than or equal to 160° C. In the rectification step, a raw material composition having an even higher content of the LC-PUFA, such as LC-PUFA alkyl ester, may be obtained.

Reverse phase distribution type column chromatography is preferred as the column chromatography. The reverse phase column chromatography may be reverse phase column chromatography that is known in the art, and high-performance liquid chromatography (HPLC) using a base material modified with octadecylsilyl groups (ODS) as a stationary phase is particularly preferable.

The composition obtained by the concentration or isolation step is a composition having a high content of the target LC-PUFA and, for example, the content of the target LC-PUFA may be 80.0% or greater, 85.0% or greater, 90.0% or greater, 95.0% or greater, 97.0% or greater, 98.0% or greater, 99.0% or greater, or 99.5% or greater, of the fatty acids. This composition containing a high concentration of LC-PUFA can be used as a raw material composition.

In the step of performing hydrolysis treatment, a reaction solution prepared by combining the provided raw material composition, the lower alcohol, the water having the total content of the metal of 0.01 ppm or less, and the alkali catalyst is used, and this reaction solution is subjected to the hydrolysis treatment. In the present specification, this hydrolysis treatment with an alkali catalyst may be referred to as alkali hydrolysis treatment.

The reaction solution used in the alkali hydrolysis treatment corresponds to the reaction solution prepared by combining the raw material composition, the lower alcohol, the water having the total content of the metal of 0.01 ppm or less, the alkali catalyst and, as necessary, other components.

The raw material composition may be a bio-oil or may be an LC-PUFA alkyl ester-containing composition. The concentration (w/w) of the raw material composition in the reaction solution may be from 10.0 wt. % to 70.0 wt. %, from 20.0 wt. % to 60.0 wt. %, or from 40 wt. % to 50 wt. %, from the perspective of reaction efficiency.

Examples of the lower alcohol include lower alcohols typically used for decomposing bio-oils or fatty acid alkyl esters to obtain free fatty acids, such as lower alcohols having from 1 to 3 carbons. The amount of the lower alcohol in the reaction solution needs to be an amount that is effective in decomposing a fatty acid in the raw material composition into a free fatty acid. For example, the amount may be from 0.9 equivalents to 32.0 equivalents, from 0.92 equivalents to 20.0 equivalents, from 0.95 equivalents to 14 equivalents, from 2.0 equivalents to 10.0 equivalents, from 3.0 equivalents to 7.0 equivalents, or from 4.5 equivalents to 5.5 equivalents, relative to the amount of the fatty acids in the composition. When the ratio of the lower alcohol to the fatty acids in the raw material composition is 0.9 equivalents or greater, the reaction tends to proceed at a more favorable rate, and suppression of generation of the coloring substance tends to be facilitated. On the other hand, when the ratio is 32.0 equivalents or less, the condition after the termination of the reaction tends to be stabilized, and progression of reverse reaction that may generate fatty acid alkyl esters tends to be effectively suppressed. The amount of the lower alcohol in the reaction solution includes both the amount of the lower alcohol added during the preparation of the reaction solution and the amount of the lower alcohol that is produced during the reaction as a byproduct in the reaction solution. In the present specification, "equivalent" refers to "molar equivalent". This is the same hereafter.

The amount of the lower alcohol in the reaction solution may be from 0.20 to 8.20, from 0.23 to 4.50, from 0.25 to 3.50, from 0.60 to 2.50, or from 1.20 to 1.50, in terms of weight ratio relative to the amount of water. When the weight ratio of lower alcohol to water is in this range, the alkali hydrolysis proceeds even more favorably, the condition after the termination of the reaction tends to be stabilized, and progression of reverse reaction that may generate fatty acid alkyl esters tends to be effectively suppressed. The amount of the lower alcohol in the reaction solution includes both the amount of the lower alcohol added during the preparation of the reaction solution and the amount of the lower alcohol that is produced during the reaction as a byproduct in the reaction solution.

The water used to prepare the reaction solution is water having the total content of the metal of 0.01 ppm or less. When the metal is explained by using iron as a representative example, tap water does not correspond to "water" in the manufacturing method of the present embodiment because the tap water typically contains 0.3 ppm of iron.

The content of the iron in the water according to another embodiment is 0.01 ppm or less, 0.005 ppm or less, or 0, that is, the water containing no iron. Typically, the value of tap water standard of the tap water in Japan is typically 0.3 ppm in terms of iron amount. In many cases in the European Union (EU), United States, and World Health Organization (WHO), the value of tap water standard is often from 0.2 to 0.3 ppm. It is considered that, when water of this level of iron concentration is used for reaction, a part of iron remains in the polyunsaturated fatty acid-containing composition after the hydrolysis, and polyunsaturated fatty acid having sufficiently low iron concentration cannot be obtained. In addition, metal pipes are typically used in an actual factory or plant of the polyunsaturated fatty acid-containing composition, and metals such as iron derived from the pipes may be mixed. Therefore, suppression of the total content of the metal, representatively the content of iron, contained in the water used in the reaction to 0.01 ppm or less may have important significance.

Examples of the water having such an iron content typically include purified water, such as ion-exchanged water, distilled water, reverse osmosis (RO) water, pure water, and ultra pure water. In the present specification, "purified water" means the water that has been purified as described above. When the water having the total content of the metal of 0.01 ppm or less, i.e. purified water, is used, a free LC-PUFA-containing composition with small variation in physical properties can be efficiently obtained.

The amount of the reaction solution in water may be from 6.0 equivalents to 13.0 equivalents, from 7.0 equivalents to 12.0 equivalents, from 8.0 equivalents to 11.0 equivalents, or from 9.0 equivalents to 10.0 equivalents, relative to the amount of the fatty acids in the raw material composition. When the weight ratio of water to raw material composition is in this range, the alkali hydrolysis can be more favorably proceeded.

The alkali catalyst used in the alkali hydrolysis treatment may be an alkali metal hydroxide, may be sodium hydroxide, potassium hydroxide, or the like, may be at least one selected from the group consisting of sodium hydroxide and potassium hydroxide, and is more preferably sodium hydroxide. The amount of the alkali catalyst used in the alkali hydrolysis treatment needs to be in a range that can produce a free fatty acid from the raw material composition. For example, the amount may be from 1.0 equivalent to 2.3 equivalents, from 1.0 equivalent to 2.0 equivalents, or from 1.0 equivalent to 1.5 equivalents, relative to the amount of the fatty acids in the raw material composition. When the ratio of the alkali catalyst to the raw material composition is in this range, reaction can be efficiently proceeded to obtain the free LC-PUFA.

The reaction solution may contain a component other than the substances described above in the range that does not impair progression of the alkali hydrolysis reaction. Examples of the component include antioxidants, such as tocopherol, vitamin C, and vitamin C derivatives, and non-alcohol solvents, such as acetone.

The hydrolysis treatment in an embodiment of the present manufacturing method needs to be performed at a temperature that can proceed the target hydrolysis treatment and, for example, may be performed at a temperature condition of 100° C. or lower, 80° C. or lower, 50° C. or lower, or 10° C. or lower. The hydrolysis treatment according to an embodiment can be performed at a temperature condition of 10° C. or lower. Because the hydrolysis treatment is performed at 10° C. or lower, generation or increase of impurities such as conjugated unsaturated fatty acids during the hydrolysis step can be suppressed. From the perspective of suppressing generation or increase of impurities such as conjugated unsaturated fatty acids, the temperature condition of the hydrolysis treatment may be, for example, −20° C. or higher, −10° C. or higher, −5° C. or higher, −4° C. or higher, −2° C. or higher, 0° C. or higher, or 2° C. or higher. The temperature range of the hydrolysis treatment may be a numerical range of a combination of any upper limit value and any lower limit value described above. For example, the temperature range may be from −20° C. to 100° C., from −10° C. to 80° C., from −5° C. to 70° C., from −4° C. to 50° C., from 0° C. to 10° C., from 0° C. to 8° C., or from 2° C. to 7° C. It is particularly preferable to perform the hydrolysis treatment in such a temperature condition at 10° C. or lower because generation or increase of the impurity described above can be further suppressed.

The reaction time of the alkali hydrolysis treatment differs depending on the set temperature range and, for example, the reaction time may be from 30 minutes to 600 hours, from 1 hour to 100 hours, from 8 hours to 80 hours, or from 19 hours to 25 hours. The amount of the fatty acid alkyl ester in the reaction solution decreases as the alkali hydrolysis treatment proceeds. Therefore, the alkali hydrolysis treatment can be terminated depending on the amount of the fatty acid alkyl ester remaining in the reaction solution. The amount of the fatty acid alkyl ester in the reaction solution can be identified by thin-layer chromatography (TLC), high performance liquid chromatography (HPLC), or the like.

The alkali hydrolysis treatment can be terminated by adding an acid to the reaction solution. By the addition of the acid, the pH of the reaction solution becomes acidic. Thus, the progression of the hydrolysis reaction is terminated, and a saponified product produced by the addition of the alkali catalyst is decomposed, thereby obtaining a free fatty acid. At this time, the free fatty acid, which is obtained by the termination treatment of the reaction, can be extracted by allowing an organic solvent such as hexane to be present in the reaction solution. Temperature conditions of the reaction termination and the extraction treatment are not particularly limited and, for example, the temperature conditions may be in a range of 0° C. to 40° C., 5° C. to 35° C., or 15° C. to 30° C. Timing of the reaction termination and the extraction treatment are not particularly limited and may be at the time when the reaction solution mixed by agitation or the like is separated into layers and stabilized.

The acid used for the termination of the alkali hydrolysis reaction is publicly known in the art, and examples of the acid include inorganic acids, such as hydrochloric acid, sulfuric acid, phosphoric acid, nitric acid, and carbonic acid, or organic acids, such as acetic acid, citric acid, and oxalic acid. As the acid, an inorganic acid is preferable from the perspective of ease in removal by water washing due to its high solubility to water. In particular, the acid is more preferably hydrochloric acid or the like because the amount of addition needs to be only a small amount and because generated salts and remaining acid can be removed. The added amount of the acid needs to be an amount that is effective in terminating the alkali hydrolysis treatment and may be approximately 1.1 equivalents relative to the amount of the added alkali catalyst.

The pH of the reaction solution after the acid addition needs to be a pH that can terminate the alkali hydrolysis, and the lower limit value thereof may be pH 0.1, pH 1.0, pH 1.5, or pH 2.0 while the upper limit value thereof may be pH 6.0, pH 5.0, pH 4.5, or pH 4.0. The pH of the reaction solution after the acid addition may be, for example, from pH 0.1 to pH 6.0, from pH 1.0 to pH 6.0, from pH 1.5 to pH 4.5, from pH 2.0 to pH 5.0, and from pH 2.0 to pH 4.0.

The reaction composition after the hydrolysis treatment contains the free LC-PUFA. The inventors first found that the free LC-PUFA elutes a metal easier compared to an unsaturated fatty acid having a short chain length, or a saturated fatty acid having a similar chain length or a monovalent monounsaturated fatty acid having a smaller degree of unsaturation. The inventors of the present disclosure further found that, by limiting the contact between the reaction composition after the hydrolysis treatment and the metal to a certain degree or less, increase of content of a metal, such as iron, that can be contained in the free polyunsaturated fatty acid-containing composition can be suppressed, and effects on physical and chemical properties and stability of the free polyunsaturated fatty acid-containing composition due to the metal can be suppressed.

In the present embodiment, the contact between this reaction product after the hydrolysis treatment and the metal is limited so that the product T ($cm^2 \times$ day) of the contact surface area ($cm^2$) per 1 g of the composition and the metal and the contact time (day) becomes 100 or less. By this, the free LC-PUFA-containing composition that efficiently suppresses the total content of the metal in the free LC-PUFA-containing composition to be in a predetermined range, e.g. 0.1 ppm or less, and that has stable physical properties can be provided.

The product T ($cm^2 \times day$) of the contact surface area ($cm^2$) per 1 g of the composition and the metal and the contact time (day) for the reaction composition after the hydrolysis treatment can be thought as the amount of the contact that is required to elute the metal that corresponds to 0.1 ppm of the total content of the metal in the composition, and is determined by elution test of iron by using the stainless steel (SUS) sphere described below.

In a 10 mL glass vial, 50 stainless steel spheres SUS 304-1/5 (diameter: ⅛ inches, formed from SUS 304) are placed. Thereafter, 5 g of the test composition is added to completely immerse the SUS spheres, and this is stored in a nitrogen atmosphere at 40° C. After the start of storage, 1 g of the composition is sampled over time, and change in the iron content is studied.

The measurement of the iron content is performed by atomic absorption spectrometry (graphite furnace method). The iron content in the test composition is determined from the iron content of the sample solution. The rate of iron elution ($ng/cm^2/day$) per 1 $cm^2$ of the contact area with the SUS is calculated to determine the product T ($cm^2 \times day$) of the contact surface area ($cm^2$) per 1 g of the composition and the metal and the contact time (day).

The obtained product T varies depending on the type and the content of the LC-PUFA in the free LC-PUFA-containing composition, and the like. The contact between the free LC-PUFA-containing composition and the metal needs to be within the range of the product T. The "product T" is the product of the contact time and the area between the composition and the metal surface per 1 g of the composition. Thus, adjust at least one of the size of the metal surface to be brought into contact and the contact time can limit the product T to be within the range.

For example, this limitation can be achieved by changing the material of the facility and apparatus to be used in the hydrolysis treatment to a nonmetal such as glass, by decreasing the size of the metal surface when the free LC-PUFA-containing composition comes into contact with the metal surface during hydrolysis treatment, in between the hydrolysis treatment and the following process, or during the storage, by decreasing the contact time with the metal surface to be brought into contact, by decreasing the size of the metal surface and decreasing the contact time, or the like. When the contact between the free LC-PUFA-containing composition and the metal surface is limited to be within the product T, for example, a free LC-PUFA-containing composition exhibiting stable physical properties before and after the hydrolysis treatment can be provided. Furthermore, for example, when the free LC-PUFA-containing composition is used as an added component, a free LC-PUFA-containing composition having stable physical properties can be provided.

The value of the product T differs depending on the type of the LC-PUFA in the free LC-PUFA-containing composition but may be 100 or less, 90 or less, 80 or less, 75 or less, 70 or less, 65 or less, 60 or less, 55 or less, 50 or less, 45 or less, or 40 or less. By using the product T within this range as a standard, the amount of the metal mixed in the composition containing the free LC-PUFA having 20 or more carbons can be efficiently suppressed to be within a predetermined range.

The metal surface that limits the contact to be within the product T relative to the free LC-PUFA-containing composition is exemplified by metals that can be eluted by the contact with the LC-PUFA. Examples thereof include iron, stainless steel, steel, tin plate, steel that is coated with, for example, zinc phosphate, and the like. Particular examples include steel, stainless steel and the like.

The duration, in which the contact between the composition and the metal surface is limited to be within the product T, may be from the start of the hydrolysis treatment until the storage in the final product container. A particular example of the duration includes from the termination of the hydrolysis treatment reaction, recovery and water washing of the free polyunsaturated fatty acid-containing composition, and storage after a solvent remover is further used, until the free polyunsaturated fatty acid-containing composition is stored in a product container.

This manufacturing method may include a washing step of removing a water-soluble component from the reaction solution obtained after the reaction termination and the extraction treatment. In the washing step, water or the like may be used as a wash liquid and added to the reaction solution. The washing step may be performed until the pH of the wash liquid used in the washing treatment reaches approximately neutral, for example, greater than 6. The temperature of the washing step is not particularly limited, and the washing step may be performed at 25° C. or lower. After the washing step, this manufacturing method may include a recovery step that recovers the target free LC-PUFA-containing composition from the organic layer of the reaction solution after the washing treatment. The recovering treatment may employ techniques typically used for this purpose and, for example, may use an evaporator or the like.

In the free LC-PUFA-containing composition obtained by an embodiment of the present manufacturing method, the total content of the metal is 0.1 ppm or less, 0.05 ppm or less, 0.03 ppm or less, or 0.01 ppm or less, and the content of the LC-PUFA may be, for example, 80.0% or greater, 85.0% or greater, 90.0% or greater, 95.0% or greater, 97.0% or greater, 98.0% or greater, 99.0% or greater, or 99.5% or greater, of the fatty acids in the composition.

The free LC-PUFA-containing composition obtained by the manufacturing method according to an embodiment has the total content of the metal and the content of the LC-PUFA as described above, and the free LC-PUFA-containing composition may have the content of the conjugated unsaturated fatty acid of 1.2% or less, 1.0% or less, 0.8% or less, 0.7% or less, 0.6% or less, 0.5% or less, 0.4% or less, or 0.3% or less, of the fatty acids in the composition.

The free LC-PUFA-containing composition obtained by the manufacturing method according to another embodiment may have the predetermined peroxide value and anisidine value described above, and the like.

The free LC-PUFA-containing composition has a smaller amount of remaining enzyme that has undergone heat inactivation treatment compared to the amount in a free LC-PUFA-containing composition obtained by using a hydrolysis enzyme. Effect of the remaining enzyme can be reduced with the composition having a smaller amount the remained heat-inactivated enzyme.

The free LC-PUFA-containing composition can have a low amount of residual organic solvent because the free LC-PUFA-containing composition is derived from a bio-oil and can be obtained without undergoing a step of chemical synthesis. The organic solvent in the present specification means an organic solvent other than fatty acids and means a hydrophobic or hydrophilic solvent having at least one carbon. Examples of the organic solvent include polar solvents, nonpolar solvents, water-miscible solvents, water-immiscible solvents, and combinations or at least two of these. Examples of the organic solvent include substituted or unsubstituted, saturated or unsaturated aliphatic hydrocarbons, aromatic hydrocarbons, alcohols, ethers, ketones, aldehydes, carboxylic acids, esters, nitriles, amides and the like. The organic solvent may be one type of these or a combination of at least two of these.

The total content of the residual organic solvent in the free LC-PUFA-containing composition may be 5000 ppm or less, 3000 ppm or less, 2000 ppm or less, or 1000 ppm or less.

The free LC-PUFA-containing composition may have a low content of at least one selected from the group consisting of methanol, ethanol, acetone, and hexane among the residual organic solvents. The content of these organic solvent may be each independently 500 ppm or less, 300 ppm or less, or 200 ppm or less. For example, all of the contents of methanol, ethanol, acetone, and hexane in the free LC-PUFA-containing composition may be 500 ppm or less, 300 ppm or less, or 200 ppm or less.

Because the free LC-PUFA-containing composition contains a high concentration of at least one free LC-PUFA and has stable physical properties, functions corresponding to the type of the LC-PUFA to be contained can be favorably exhibited at high levels, and the free LC-PUFA-containing composition can be suitably used for various purposes while excellent handling is made possible.

Examples of preferable applications of the free LC-PUFA-containing composition include usage in food products, supplements, medicaments, cosmetics, and animal feed and usage in the manufacturing methods therefor. In particular, the free LC-PUFA-containing composition may be preferably used in medicaments containing a composition containing the LC-PUFA as an active ingredient. For example, when this free LC-PUFA-containing composition is a composition containing free ARA, free DGLA, free EPA, free DHA, or the like, the free LC-PUFA-containing composition can be significantly advantageously applied for the purposes requiring high productivity and high content of these functional LC-PUFA. Examples of such purposes include food products, supplements, medicaments, cosmetics, and animal feed that are expected to exhibit effect on prevention of lifestyle-related diseases, such as arteriosclerosis, cerebral infarction, myocardial infarction, thrombosis, and hyperlipemia, improvement of metabolic syndrome, antiallergy, antiinflammation, anticancer, improvement in brain functions although such examples vary depending on the type of the LC-PUFA in the composition. Examples of the medicament include external medicines for skin, oral preparations and the like.

When the free LC-PUFA-containing composition is used as a medicament, the medicament contains the free LC-PUFA-containing composition and a pharmaceutically acceptable carrier and, as necessary, other components. The dosage form may be any form that is convenient for oral administration or parenteral administration based on the type of the LC-PUFA in the composition. Examples of the dosage form include injections, transfusions, powders, granules, tablets, capsules, enteric coated tablets, troches, peroral liquid preparations, suspensions, emulsions, syrups, liquids for external use, fomentations, nasal preparations, eardrops, eye drops, inhalants, ointments, lotions, suppositories and the like. These may be used individually or in combination depending on the symptoms.

By normal methods, these various types of preparations, according to a purpose, may be formulated by adding, to the principle agent, previously known adjutants commonly used in the field of drug preparation technology, as exemplified by excipients, binders, preservatives, stabilizers, disintegrants, lubricants, flavoring agents, or the like. Furthermore, in the case of oral administration for an adult, typically, the dosage for administration can be appropriately adjusted in a range of 0.01 mg to 10 g, preferably 0.1 mg to 2 g, and more preferably 1 mg to 200 mg, per day as the total amount of the LC-PUFA as a structured lipid. In the case of parenteral administration, the dosage for administration can be appropriately adjusted in a range of 0.001 mg to 1 g, preferably 0.01 mg to 200 mg, and more preferably 0.1 mg to 100 mg, per day as the total amount of the LC-PUFA as a structured lipid. However, these dosages differ depending on purpose of the administration, type of the LC-PUFA in the composition, and conditions of the person subjected to the administration (sex, age, weight, and the like).

The storing method of the free LC-PUFA-containing composition according to an embodiment maintains in a condition that limits contact with metal so that the product T ($cm^2 \times day$) of the contact surface area ($cm^2$) per 1 g of the composition and the metal and the contact time (day) becomes 100 or less.

Because the storing method of the free LC-PUFA-containing composition according to the present embodiment limits contact with the metal of the free LC-PUFA-containing composition so that the product T ($cm^2 \times day$) of the contact surface area ($cm^2$) per 1 g of the composition and the metal and the contact time (day) becomes 100 or less, the content of the iron in the free LC-PUFA-containing composition can be efficiently suppressed to a predetermined amount or less, e.g. 0.1 ppm or less. As a result, unexpected conditions such as variation in the physical properties of the free LC-PUFA-containing composition during the storage can be avoided. Furthermore, the free LC-PUFA-containing composition stored by the storing method according to the present embodiment can be used for various purposes, after the storage, as an added component with which excellent handling is possible and, for example, can be used as a component for food products, supplements, medicaments, cosmetics, animal feed, and the like.

Regarding the storage method of the free LC-PUFA-containing composition according to the present embodiment, for the limiting condition of the contact with metal, descriptions for the manufacturing method of the free LC-PUFA-containing composition according to another embodiment are applicable.

EXAMPLES

The present disclosure is described below in detail using examples. However, the present disclosure is not limited in any manner by these examples.

In the examples and comparative examples in the section below, the LC-PUFA refers only to particular types; however, the type of the LC-PUFA is not particularly limited.

It was supposed that most of the fatty acids contained in the fatty acid alkyl ester-containing composition used in the examples as a raw material composition is in a fatty acid alkyl ester form. Consequently, the fatty acids contained in the samples are all described below as fatty acids in the alkyl ester form. However, this does not completely negate the fact that fatty acids in a form other than an alkyl ester form are included.

Example 1

Using purified water that contained substantially no iron (iron content: 0.01 ppm or less), an EPA ethyl ester 1 that contained 96.8% of EPA and that was derived from a fish oil was subjected to hydrolysis by using an alkali catalyst at a relatively high temperature.

That is, 5.0 g of EPA ethyl ester 1 was poured in a glass eggplant-shaped flask, then 3.5 mL (4.0 equivalents relative to the amount of the fatty acids) of ethanol, 2.0 mL of purified water, and 1.5 g of 48 wt. % sodium hydroxide aqueous solution (1.2 equivalents of NaOH relative to the amount of the fatty acids; ethanol-water weight ratio: 0.4) were added thereto to prepare a sample solution 1. The sample solution 1 in the eggplant-shaped flask was agitated at 70° C. for 24 hours while being heated in an oil bath to perform hydrolysis treatment.

The purified water was obtained by treating tap water by the next-generation Water Purifier Autopure WEX 5 (manufactured by Yamato Scientific Co., Ltd.) and then by the pure water-supplying type Water Purification System Synergy UV (Millipore Corporation). The specific resistance value of the obtained purified water was 18.2 MΩ·cm, and the content of the iron was 0.1 ppm or less. This is the same hereafter.

The termination of the hydrolysis treatment reaction was determined as follows.

That is, a part of the sample solution 1 was taken out and combined and mixed in the ratio, sample solution:1N hydrochloric acid aqueous solution:hexane=1:2:5 (v/v/v). The separated hexane layer was used as a sample for identification.

Onto a TLC plate, 0.5 μL of the sample for identification was loaded by using a microsyringe and developed in a developing chamber. After the development, the thin-layer plate was taken out from the developing chamber, the solvent was vaporized in a fume hood, and a p-anisaldehyde coloring reagent was applied by dipping. After the application, heating was performed at approximately from 110° C. to 120° C. until color developed, thereby obtaining a spot. Disappearance of the spot of the raw material ethyl ester was visually observed and used as the point of reaction termination. This is the same hereafter.

As the development solvent, a solvent in which hexane:diethylether:acetic acid was 80:20:1 (v/v/v) was used. As the TLC plate, Silica gel 60G F254 (Merck Millipore) was used. As the coloring agent, a p-anisaldehyde coloring reagent was used.

The p-anisaldehyde coloring reagent was prepared as described below. That is, after 9.3 mL of p-anisaldehyde, 3.8 mL of acetic acid, and 340 mL of ethanol were mixed while being cooled with ice, 12.5 mL of concentrated sulfuric acid was mixed to the mixture to prepare the p-anisaldehyde coloring reagent.

The sample solution 1 after the treatment was air-cooled and transferred into a glass separatory funnel, and then 6.3 mL of hexane and 5.0 mL of purified water were added to this sample solution 1. Further, 2.1 g of hydrochloric acid was added and agitated, and then allowed to stand still. Thereafter, the sample solution 1 was separated into two layers, a hexane layer and an aqueous layer. The pH of the aqueous layer was 0.4.

After the aqueous layer was removed from the sample solution 1, 7.5 mL of purified water was further added to the sample solution 1 and agitated. An extremely small amount of hydrochloric acid was added to adjust the pH of the aqueous layer to 0.1, and then the bottom layer was removed. Thereafter, water washing was performed by using the same amount of purified water as a liquid for water washing. When an emulsion was formed after the purified water was added and thus sufficient separation was not possible, water washing was performed by using a liquid for water washing prepared by adding a small amount of common salt into purified water. Water washing was repeated until the liquid for water washing collected after the water washing became neutral (pH 3.5 or higher). The hexane layer was recovered from the sample solution 1 after the water washing and placed in another glass eggplant-shaped flask. From the recovered hexane layer, hexane was removed by an evaporator and vacuum drawing, and 4.3 g of EPA 1, which was a composition containing free EPA, was obtained.

Example 2

Using purified water that contained substantially no iron (iron content: 0.01 ppm or less), a DGLA ethyl ester 2 that contained 95.8% of DGLA and that was derived from a microorganism was subjected to hydrolysis by using an alkali catalyst at a relatively high temperature.

That is, 3.0 g of DGLA ethyl ester 2 was poured in a glass eggplant-shaped flask, then 2.1 mL (4.0 equivalents relative to the amount of the fatty acids) of ethanol, 1.2 mL of purified water, and 0.9 g of 48 wt. % sodium hydroxide aqueous solution (1.2 equivalents of NaOH relative to the amount of the fatty acids; ethanol-water weight ratio: 0.4) were added thereto to prepare a sample solution 2. The sample solution 2 in the eggplant-shaped flask was agitated at 70° C. for 24 hours while being heated by an oil bath to perform hydrolysis treatment.

The sample solution 2 after the treatment was air-cooled and transferred into a glass separatory funnel, and then 3.8 mL of hexane and 3.0 mL of purified water were added to this sample solution 2. Further, 1.3 g of hydrochloric acid was added and agitated, and then allowed to stand still. Thereafter, the sample solution 2 was separated into two layers, a hexane layer and an aqueous layer. The pH of the aqueous layer was 2.1.

After the aqueous layer was removed from the sample solution 2, 4.5 mL of purified water was further added to the sample solution 2 and agitated. An extremely small amount of hydrochloric acid was added to adjust the pH of the aqueous layer to 1.4, and then the bottom layer was removed. Thereafter, water washing was performed by using the same amount of purified water as a liquid for water washing. When an emulsion was formed after the purified water was added and thus sufficient separation was not possible, water washing was performed by using a liquid for water washing prepared by adding a small amount of common salt into purified water. Water washing was repeated until the liquid for water washing collected after the water washing became neutral pH (pH 3.5 or higher). The hexane layer was recovered from the sample solution 2 after the water washing and placed in another glass eggplant-shaped flask. Hexane was removed from the recovered hexane layer by an evaporator and vacuum drawing, and 2.5 g of DGLA 2, which was a composition containing free DGLA, was obtained.

Example 3

Using purified water that contained substantially no iron (iron content: 0.01 ppm or less), an DHA ethyl ester 3 that contained 97.6% of DHA and that was derived from fish oil was subjected to hydrolysis by using an alkali catalyst at a relatively high temperature.

That is, 3.0 g of DHA ethyl ester 3 was poured in a glass eggplant-shaped flask, then 2.1 mL (4.3 equivalents relative to the amount of the fatty acids) of ethanol, 1.2 mL of purified water, and 0.9 g of 48 wt. % sodium hydroxide aqueous solution (1.3 equivalents of NaOH relative to the amount of the fatty acids; ethanol-water weight ratio: 0.4) were added thereto to prepare a sample solution 3. The sample solution 3 in the eggplant-shaped flask was agitated at 70° C. for 24 hours while being heated in an oil bath to perform hydrolysis treatment.

The sample solution 3 after the treatment was air-cooled and transferred into a glass separatory funnel, and then 3.8 mL of hexane and 3.0 mL of purified water were added to this sample solution 3. Further, 1.3 g of hydrochloric acid was added and agitated, and then allowed to stand still. Thereafter, the sample solution 3 was separated into two layers, a hexane layer and an aqueous layer. The pH of the aqueous layer was 1.1.

After the aqueous layer was removed from the sample solution 3, 4.5 mL of purified water was further added to the sample solution 3 and agitated. An extremely small amount of hydrochloric acid was added to adjust the pH of the aqueous layer to 0.1, and then the bottom layer was removed. Thereafter, water washing was performed by using the same amount of purified water as a liquid for water washing. When an emulsion was formed after the purified water was added and thus sufficient separation was not possible, water washing was performed by using a liquid for water washing prepared by adding a small amount of common salt into purified water. Water washing was repeated until the liquid for water washing collected after the water washing became neutral pH (pH 3.5 or higher). The hexane layer was recovered from the sample solution 3 after the water washing and placed in another glass eggplant-shaped flask. Hexane was removed from the recovered hexane layer by an evaporator and vacuum drawing, and 2.5 g of DHA 3, which was a composition containing free DHA, was obtained.

Example 4

Using purified water that contained substantially no iron (iron content: 0.01 ppm or less), an EPA ethyl ester 4 that contained 96.8% of EPA and that was derived from fish oil was subjected to hydrolysis by using an alkali catalyst at a low temperature.

That is, 3.0 g of EPA ethyl ester 4 was poured in a glass eggplant-shaped flask, then 2.1 mL (4.0 equivalents relative to the amount of the fatty acids) of ethanol, 1.2 mL of purified water, and 0.9 g of 48 wt. % sodium hydroxide aqueous solution (1.2 equivalents of NaOH relative to the amount of the fatty acids; ethanol-water weight ratio: 0.4) were added thereto to prepare a sample solution 4. The sample solution 4 in the eggplant-shaped flask was agitated at 6° C. for 24 hours while being cooled to perform hydrolysis treatment.

The sample solution 4 after the treatment was transferred into a glass separatory funnel, and then 3.8 mL of hexane and 3.0 mL of purified water were added to this sample solution 4. Further, 1.3 g of hydrochloric acid was added and agitated, and then allowed to stand still. Thereafter, the sample solution 4 was separated into two layers, a hexane layer and an aqueous layer. The pH of the aqueous layer was 0.9.

After the aqueous layer was removed from the sample solution 4, 4.5 mL of purified water was further added to the sample solution 4 and agitated. An extremely small amount of hydrochloric acid was added to adjust the pH of the aqueous layer to 0.6, and then the bottom layer was removed. Thereafter, water washing was performed by using the same amount of purified water as a liquid for water washing. When an emulsion was formed after the purified water was added and thus sufficient separation was not possible, water washing was performed by using a liquid for water washing prepared by adding a small amount of common salt into purified water. Water washing was repeated until the liquid for water washing collected after the water washing became neutral pH (pH 3.5 or higher). The hexane layer was recovered from the sample solution 4 after the water washing and placed in another glass eggplant-shaped flask. Hexane was removed from the recovered hexane layer by an evaporator and vacuum drawing, and 2.4 g of EPA 4, which was a composition containing free EPA, was obtained.

Evaluation 1: Confirmation of Iron Content and Confirmation of Product T

For the EPA-containing composition obtained in Example 1 and the DGLA-containing composition obtained in Example 2, the iron contents and the acceptable values of contact T were determined as described below.

As the target, oleic acids (reagent: oleic acid content: 68%; other fatty acids 3 wt. % of C14:0; 3 wt. % of C16:0; 5 wt. % of C16:1; 4 wt. % of C18:1, n-7; 5 wt. % of C18:2, n-6; Wako 1st Grade; manufactured by Wako Pure Chemical Industries, Ltd.) were used. Note that, as described above, in Examples 1 and 2, glass apparatus was used throughout the hydrolysis treatment, the hexane extraction, and the recovery of the composition, and almost no contact with metal surfaces occurred.

In a 10 mL glass vial (SV-10, manufactured by Nichiden Rika Glass Co., Ltd.), 50 stainless steel spheres SUS 304-1/5 (diameter: ⅛ inches, formed from SUS 304, manufactured by AS ONE Corporation) were placed. Thereafter, 5 g of the test composition was added to completely immerse the SUS spheres, and this was stored in a nitrogen atmosphere at 40° C. After 5 days and 9 days, 1 g was sampled over time, and change in the iron content was studied.

In the cases of the LC-PUFA-containing compositions of Examples 1 and 2, samples obtained by being further purified with silica gel after the hydrolysis treatment and subjected to removal of a small amount of oxide products were used.

The total surface area of the 50 SUS spheres was calculated from the following equation and was 15.8 cm².

$$\text{The total surface area (cm}^2\text{)} = 50 \times 4 \times 3.14 \times (\tfrac{1}{8} \times 2.54/2)^2$$

The change in the iron content in the test composition was determined by atomic absorption spectrometry (graphite furnace method) in the following conditions.

After 1 g of the test composition was weighed and 0.15 mL of nitric acid (for measuring harmful metals, manufactured by Wako Pure Chemical Industries, Ltd.) was added thereto, the mixture was diluted with methyl isobutyl ketone (for atomic absorption spectrometry, manufactured by Wako Pure Chemical Industries, Ltd.) in a volumetric flask to 10 mL total and used as a sample solution.

The reference sample was Conostan S-21 (10 ppm (wt.)). This reference sample was diluted with methyl isobutyl ketone to prepare calibration curve samples (0 μg/L, 10 μg/L, and 20 μg/L).

For the iron quantitation by the graphite furnace method via an analytical instrument by using the sample solution and the reference samples, the atomic absorption spectrometry was performed in the following analytical conditions. The iron content in the sample solution was quantitated by automatic calculation by the software provided with the instrument.

Instrument: Z-2000, Zeeman Atomic Absorption Spectrophotometer (Hitachi, Ltd.)
Injection amount: 20 μL
Measurement mode: graphite atomizer/autosampler
Measured element: Fe
Cuvette: Pyro tube HR
Measured wavelength (nm): 248.3
Measurement signal: BKG correction
Slit width (nm): 0.2
Time constant (s): 0.1
Lamp current (mA): 12.5
Heat control method: light temperature control
Temperature Program
  1 Drying: from 80° C. to 140° C.; time for temperature increase: 40 seconds; retention time: 0 seconds; gas flow rate: 200 mL/min
  2 Ashing: at 1000° C.; time for temperature increase: 20 seconds; retention time: 0 seconds; gas flow rate: 200 mL/min
  3 Atomization: at 2400° C.; time for temperature increase: 0 seconds; retention time: 5 seconds; gas flow rate: 30 mL/min
  4 Cleaning: at 2700° C.; time for temperature increase: 0 seconds; retention time: 4 seconds; gas flow rate: 200 mL/min 5 Cooling: at 0° C.; time for temperature increase: 0 seconds; retention time: 10 seconds; gas flow rate: 200 mL/min The iron content of the EPA 1 was calculated based on the following Equation (3) from the iron content of the sample solution that had been subjected to the quantitation.

$$\text{The iron content in the EPA 1 [ppm]} = C/(W \times 100) \quad (3)$$

In the equation, C represents the iron content (μg/L) of the sample solution obtained by the atomic absorption spectrometry, and W represents the sampled amount (g) of the EPA 1.

The rate of elution of the iron (ng/cm²/day) in the case where 1 g of the composition was brought into contact with 1 cm² of SUS was determined from the obtained iron amount. The results are shown in Table 1.

TABLE 1

| Type of fatty acid | Iron content (ppm) | | | Rate of iron elution (ng/cm²/day) | Product T (cm² × day) |
|---|---|---|---|---|---|
| | 0th day | 5th day | 9th day | | |
| Example 1 (EPA) | 0.00 | 0.21 | 0.37 | 2.6 | 38 |
| Example 2 (DGLA) | 0.01 | 0.17 | 0.21 | 1.4 | 72 |
| Oleic acid | 0.01 | 0.12 | 0.14 | 0.9 | 108 |

As shown in Table 1, all of the free EPA-containing composition of Example 1 and the free DGLA-containing composition of Example 2 had the iron contents of 0.1 ppm or less. Therefore, it was found that, because both of the hydrolysis treatment and measurement for Example 1 and Example 2 were performed by using glass apparatus, such use of glass apparatus was appropriate for limiting the iron content in the composition to 0.1 ppm or less.

Furthermore, the rate of elution of the iron in the case where 1 g of the composition was brought into contact with the SUS having the contact area of 1 cm² was 2.6 ng/cm²/day for the free EPA-containing composition according to Example 1 and 1.4 ng/cm²/day for the free DGLA-containing composition according to Example 2, which were faster than 0.9 ng/cm²/day for the oleic acid. As a result, the product T was 38 (cm²×day) for the EPA-containing composition of Example 1 and 72 (cm²×day) for the DGLA-containing composition of Example 2, which were significantly smaller than 108 (cm²× day) for the oleic acid.

These results show that the EPA-containing composition and the DGLA-containing composition according to Examples 1 and 2, respectively, showed different behavior from that of the oleic acid which is an unsaturated fatty acid having 18 carbons.

Evaluation 2: Characteristics of Composition

The peroxide value, the conjugated diene content, the peroxide value, the anisidine value, the iron content, and the fatty acid composition were determined for the raw material compositions of Examples 1 to 3 (raw material EPA ethyl ester 1, raw material DGLA ethyl ester 2, raw material DHA ethyl ester 3, and raw material EPA ethyl ester 4) and the free LC-PUFA-containing compositions (EPA 1, DGLA 2, DHA 3, and EPA 4) obtained as described above in accordance with the methods described below. The evaluation results are shown in Table 2. The fatty acid compositions, the conjugated diene contents, the anisidine values, the peroxide values, and the iron contents of the raw material compositions are shown in Table 3. Conjugated unsaturated fatty acids other than the conjugated dienoic acid were not detected.

Note that, for the conjugated unsaturated fatty acid, only the conjugated dienoic acid is shown in Table 2.

(1) Peroxide Value

The peroxide value of the raw material composition and the free LC-PUFA-containing composition were measured in accordance with the ferric thiocyanate method.

That is, a chloroform/methanol solution was prepared by mixing chloroform (Guaranteed Reagent, manufactured by Wako Pure Chemical Industries, Ltd.) and methanol (Guaranteed Reagent, manufactured by Wako Pure Chemical Industries, Ltd.) in a ratio of 2:1 (vol/vol). A 30% ammonium thiocyanate aqueous solution was prepared by weighing 1.5 g of ammonium thiocyanate (Guaranteed Reagent, manufactured by Wako Pure Chemical Industries, Ltd.) and adding purified water so that the total weight thereof became 5.0 g. A 0.02 N iron(II) sulfate/3.5% hydrochloric acid was prepared by weighing, in a 10 mL volumetric flask, 27.8 mg of iron(II) sulfate (Guaranteed Reagent, manufactured by Nacalai Tesque), adding 1 mL of hydrochloric acid (Guaranteed Reagent, manufactured by Wako Pure Chemical Industries, Ltd.), further adding purified water so that the total volume thereof became 10 mL, and mixing the mixture.

In a glass test tube with a stopper, 100 mg of the sample was weighed, then 4 mL of the chloroform/methanol solution was added thereto, vigorously agitated and mixed. This mixture was used as the sample solution. The chloroform/methanol solution was used as the blank solution. In another glass test tube with a stopper, 4.55 mL of chloroform/methanol solution was poured, 0.25 mL of the sample solution or the blank solution was added, and 0.1 mL of 30% ammonium thiocyanate aqueous solution and 0.1 mL of 0.02 N iron(II) sulfate/3.5% hydrochloric acid were further added, and the mixture was immediately agitated and mixed. Accurately after 3 minutes, absorbance at 500 nm was measured to determine the absorbance of the sample reaction solution or the absorbance of the blank reaction solution. In accordance with the following Equation (2), the peroxide value was calculated from the obtained absorbance.

$$\text{Peroxide value (meq/kg)} = 30.70 \times (A1 - A0) + 0.1578 \quad (2)$$

In the equation, A1 represents the absorbance of the sample reaction solution and A0 represents the absorbance of the blank reaction solution.

In Equation (2), determination was performed by using the relation between the measurement result of the peroxide value of the oxidized soybean oil (Standard Methods for the Analysis of Fats, Oils, and Related Materials 2.5.2.1-2013) and the absorbance (A1−A0) obtained by the ferric thiocyanate method described above.

Note that, the UV-Vis spectrophotometer V-560 (manufactured by JASCO Corporation) was used for the absorbance measurement. A quartz cell having an optical path length of 10 mm was used, and the chloroform/methanol solution was used as a control.

(2) Conjugated Dienoic Acid

The measurement was performed based on Reference 1.14 of the Standard Methods for the Analysis of Fats, Oils, and Related Materials, 2013 Edition, established by Japan Oil Chemists' Society (JOCS).

(3) Anisidine Value

The anisidine value was determined based on 2.5.3 of the Standard Methods for the Analysis of Fats, Oils, and Related Materials, 2013 Edition, established by Japan Oil Chemists' Society (JOCS).

(4) Iron Content Analysis

The iron contents of the raw material composition and the free LC-PUFA-containing composition were determined by atomic absorption spectrometry (graphite furnace method) in the following conditions.

After 1 g of the raw material composition or the free LC-PUFA-containing composition was weighed and 0.15 mL of nitric acid (for measuring harmful metals, manufactured by Wako Pure Chemical Industries, Ltd.) was added thereto, the mixture was diluted with methyl isobutyl ketone (for atomic absorption spectrometry, manufactured by Wako Pure Chemical Industries, Ltd.) in a volumetric flask to 10 mL total and used as a sample solution.

The reference sample was Conostan S-21 (10 ppm (wt.)). This reference sample was diluted with methyl isobutyl ketone to prepare calibration curve samples (0 μg/L, 10 μg/L, and 20 μg/L).

For the iron quantitation by the graphite furnace method via an analytical instrument by using the sample solution and the reference samples, the atomic absorption spectrometry was performed in the following analytical conditions. The iron content in the sample solution was quantitated by automatic calculation by the software provided with the instrument.

Instrument: Z-2000, Zeeman Atomic Absorption Spectrophotometer (Hitachi, Ltd.)
Injection amount: 20 μL
Measurement mode: graphite atomizer/autosampler
Measured element: Fe
Cuvette: Pyro tube HR
Measured wavelength (nm): 248.3
Measurement signal: BKG correction
Slit width (nm): 0.2
Time constant (s): 0.1
Lamp current (mA): 12.5
Heat control method: light temperature control Temperature Program 1 Drying: from 80° C. to 140° C.; time for temperature increase: 40 seconds; retention time: 0 seconds; gas flow rate: 200 mL/min 2 Ashing: at 1000° C.; time for temperature increase: 20 seconds; retention time: 0 seconds; gas flow rate: 200 mL/min 3 Atomization: at 2400° C.; time for temperature increase: 0 seconds; retention time: 5 seconds; gas flow rate: 30 mL/min 4 Cleaning: at 2700° C.; time for temperature increase: 0 seconds; retention time: 4 seconds; gas flow rate: 200 mL/min 5 Cooling: at 0° C.; time for temperature increase: 0 seconds; retention time: 10 seconds; gas flow rate: 200 mL/min The iron content of the raw material composition or the free LC-PUFA-containing composition was calculated based on the following Equation (3) from the iron content of the sample solution that had been subjected to the quantitation.

$$\text{The iron content [ppm]} = C/(W \times 100) \quad (3)$$

In the equation, C represents the iron content (μg/L) of the sample solution obtained by the atomic absorption spectrometry, and W represents the sampled amount (g) of the raw material composition or the free LC-PUFA-containing composition.

(5) Fatty Acid Composition

The fatty acid compositions of the raw material composition and the free LC-PUFA-containing composition were determined from each fatty acid peak obtained by gas chromatography performed in the conditions described below. Note that, the free LC-PUFA-containing composition was methyl-esterified before the gas chromatography analysis. The methyl esterification was performed in accordance with American Oil Chemists' Society (AOCS) Official Method Ce 1b-89.

Gas Chromatography Analysis Conditions

Instrument: Agilent 7890 GC system (Agilent Technologies)
Column: DB-WAX (Agilent Technologies, 30 m×0.25 mm ID, 0.25 μm film thickness) J&W122-7032
Column oven: 180° C.-3° C./min-230° C. (25 min)
Injection temperature: 250° C.
Injection method: split
Split ratio: 30:1
Detector temperature: 270° C.
Detector: FID
Carrier gas: helium (1.0 mL/min, constant flow)

TABLE 2

|  | Example 1 | Example 2 | Example 3 | Example 4 |
| --- | --- | --- | --- | --- |
| Type of LC-PUFA | EPA | DGLA | DHA | EPA |
| Reaction temperature (° C.) | 70 | 70 | 70 | 6 |
| Type of reaction water | Purified water | Purified water | Purified water | Purified water |
| Amount of 48% NaOH aqueous solution (g) | 1.5 | 0.9 | 0.9 | 0.9 |
| Amount of ethanol (mL) | 3.5 | 2.1 | 2.1 | 2.1 |
| Amount of water (g) | 2 | 1.2 | 1.2 | 1.2 |
| Supplied amount of raw material composition (g) | 5 | 3 | 3 | 3 |
| Recovered amount of product (g) | 4.3 | 2.5 | 2.5 | 2.4 |
| Concentration of PUFA in fatty acid (%) | 97.4 | 95.7 | 97.7 | 97.4 |
| Conjugated dienoic acid (%) | 0.65 | 0.26 | 1.01 | 0.42 |
| Anisidine value | 1.42 | 3.15 | 1.41 | 0.88 |
| Peroxide value (meq/kg) | 2.11 | 3.3 | 1.91 | 3.35 |
| Iron content (ppm) | 0.01 | 0.05 | 0.02 | 0.00 |

TABLE 3

|  | Example 1 | Example 2 | Example 3 | Example 4 |
| --- | --- | --- | --- | --- |
| Concentration of PUFA in fatty acid (%) | 96.8 | 95.8 | 97.6 | 96.8 |
| Conjugated dienoic acid (%) | 0.35 | 0.17 | 0.49 | 0.40 |
| Anisidine value | 0.51 | 1.14 | 0.68 | 0.49 |
| Peroxide value (meq/kg) | 2.71 | 1.52 | 2.32 | 2.02 |
| Iron content (ppm) | 0.10 | 0.00 | 0.00 | 0.01 |

Evaluation 3: Solidification Temperature Evaluation

The change in the solidification temperatures in the case where the iron content was changed was evaluated by using the DGLA 2 of Example 2 (DGLA 95.8%; iron content: 0.00 ppm) as the reference free DGLA composition as described below.

(1) Effect on Solidification Temperature of DGLA-Containing Composition

An aqueous solution of iron(II) sulfate heptahydrate (Guaranteed, Nacalai Tesque) was added to the reference free DGLA composition, thereby preparing a sample having the iron content of 10 ppm. An adequate amount of ethanol was added thereto and homogenized, and then the solvent was removed by vacuum drawing. The obtained sample having the iron content of 10 ppm was diluted with the reference free DGLA-containing composition to prepare free DGLA samples each having a concentration of 0.05 ppm, 0.1 ppm, and 1 ppm.

For each sample having the concentration, the solidification temperature was measured by using experimental devices and apparatus for melting point (transparent melting point, Standard Methods for the Analysis of Fats, Oils, and Related Materials 3.2.2.1-2013) as a reference. That is, approximately 1 cm of the liquid oil was charged in a capillary tube via an apparatus similar to the apparatus for melting point measurement, and the cooling temperature was decreased by 0.5° C. every minute. The temperature at which the oil liquid in the capillary tube became white turbid was defined as the solidification temperature. The results are shown in Table 4.

(2) Effect on Solidification Temperature of Soapy Water

By using the reference free DGLA composition used in the evaluation of (1) described above, 5% soapy water and 10% soapy water of the free DGLA were prepared. The temperature at which white turbidity was observed due to crystallization or solidification was measured. The 5% soapy water was prepared by mixing 0.5 g of the reference free DGLA composition, 0.15 g of 48% sodium hydroxide aqueous solution, and 9.35 g of purified water until the mixture was homogenized. The 10% soapy water was prepared by mixing 1.0 g of the reference free DGLA composition, 0.30 g of 48% sodium hydroxide aqueous solution, and 8.70 g of purified water until the mixture was homogenized. Both the soapy waters were strongly basic and had pHs of 12 or higher.

The temperature of solidification was measured by the same method as for (1) described above. The results are shown in Table 4.

TABLE 4

| Iron content of measurement sample (ppm) | Solidification temperature (° C.) | | |
|---|---|---|---|
| | Free DGLA sample | 5% Soapy water | 10% Soapy water |
| 0 | −30.5 | −8.7 | −8.7 |
| 0.05 | −30.1 | −7.6 | −8.4 |
| 0.10 | −30.3 | −6.9 | −7.0 |
| 1.00 | −25.8 | −6.9 | −6.9 |

Table 4 shows that in all the free DGLA sample and the soapy waters of the concentrations, the solidification temperature was increased and solidification occurred more easily due to the increase in the contained iron content. In particular, the solidification temperature was significantly increased in the soapy water depending on the iron content, compared to the case of the free DGLA sample. This shows that the increase in the solidification temperature may affect the handling during processing of product formulation and/or the clogging of pipes.

Evaluation 4: Membrane Evaluation

The membrane evaluation test was performed by using the DGLA 2 of Example 2 (DGLA 95.7 wt. %; iron content: 0.00 ppm) as the reference free DGLA composition as described below. The results are shown in Table 5.

Test Method

The circular frame for test described below (see FIG. 1) was immersed in a fatty acid test solution (a reference solution or a test solution) in a condition at a temperature of 25° C., 1 atmosphere, and a relative humidity of 55%. Then, membranes were formed in the sections formed by the plurality of inner frames by gradually bringing the circular frame above a liquid surface. A time required for at least one of the formed membrane to be broken (retention time) was measured by using a stopwatch. The results are shown in Table 5. As the fatty acid test solution used herein, a reference solution or a test solution described below was used. As the circular frame for test used for the measurement, a circular frame for test described below was prepared.

Preparation of Test Solution

Reference Solution

An aqueous solution of iron(II) sulfate heptahydrate (Guaranteed, Nacalai Tesque) was added to the DGLA 2 of Example 2 so that the iron content thereof became 100 ppm. An adequate amount of ethanol was further added thereto and homogenized, and then the solvent was removed by vacuum drawing to prepare the DGLA 2 containing 100 ppm of iron. 0.5 g of this DGLA 2 containing 100 ppm of iron, 0.15 g of 48 wt. % of sodium hydroxide, and 9.35 g of purified water were mixed to obtain an aqueous solution that was derived from the DGLA 2 of Example 2 and that contained 5.1 wt. % of the DGLA sodium in the aqueous solution. The obtained aqueous solution was used as "reference solution".

Test Solution

The reference solution containing 100 ppm of iron in the DGLA 2 obtained as describe above was diluted with the DGLA 2 of Example 2 to prepare DGLA 2 having an iron content of 0.05 ppm, DGLA 2 having an iron content of 0.1 ppm, and DGLA 2 having an iron content of 1.0 ppm. 0.5 g of one of these obtained DGLA 2, 0.15 g of 48 wt. % of sodium hydroxide, and 9.35 g of purified water were mixed to prepare an aqueous solution for test containing 5.1 wt. % of the DGLA sodium. This was used as a "test solution" which was the sample for evaluation.

Preparation of Circular Frame for Test

A circular frame for test that was formed from plastic and that had one large section and four small sections divided by four inner frames having a thickness of 2 mm in an outer frame having a diameter of 64 mm, an inner diameter of 52 mm, and a thickness of 3 mm was provided (see FIG. 1).

TABLE 5

| Iron content of measurement sample (ppm) | 1% Soapy water | | 5% Soapy water | |
|---|---|---|---|---|
| | Retention time (sec) | Relative value | Retention time (sec) | Relative value |
| 0.00 | 61 ± 12 | 1.1 | 28 ± 4 | 1.6 |
| 0.05 | 62 ± 6 | 1.1 | 33 ± 7 | 1.9 |
| 0.10 | 64 ± 8 | 1.2 | 33 ± 4 | 1.9 |
| 1.00 | 69 ± 8 | 1.3 | 41 ± 8 | 2.4 |
| 100.00 | 55 ± 13 | 1.0 | 17 ± 3 | 1.0 |

Table 5 shows that the retention time varied depending on the iron content in the measurement sample, and the iron content in the composition affected the retention of the membrane.

Disclosure of JP 2015-170856 A filed on Aug. 31, 2015 is incorporated herein in its entirety by reference.

All documents, patent applications, and technical specifications stated in the present specification are incorporated by citation in the present specification to the same degree as if stated to be incorporated by reference specifically and individually.

What is claimed is:

1. A free polyunsaturated fatty acid-containing composition, (i) comprising at least one free polyunsaturated fatty acid in an amount that a content thereof is 80.0% or greater of fatty acids in the composition; (ii) having a content of the conjugated unsaturated fatty acid in the range of 0.001% to 1.2% of the fatty acids in the composition; and (iii) having a total iron content of being 0.1 ppm or less,
   wherein the polyunsaturated fatty acid is selected from the group consisting of eicosadienoic acid, dihomo-γ-linolenic acid, Mead acid, eicosatetraenoic acid, arachidonic acid, eicosapentaenoic acid, docosatetraenoic acid, docosapentaenoic acid, and docosahexaenoic acid.

2. The free polyunsaturated fatty acid-containing composition according to claim 1, wherein a peroxide value is 5.0 meq/kg or less.

3. The free polyunsaturated fatty acid-containing composition according to claim 1, wherein an anisidine value is 5.0 or less.

4. The free polyunsaturated fatty acid-containing composition according to claim 1, wherein, in a case where a membrane evaluation test described below is performed by using the free polyunsaturated fatty acid-containing composition, a time passed until a membrane formed by using a test solution prepared from the free polyunsaturated fatty acid-containing composition is broken is 1.4 or greater when a time passed until a membrane formed by using a reference solution is broken is expressed as 1;
   Membrane evaluation test:
   a circular frame for the membrane evaluation test, the circular frame having a plurality of inner frames, is immersed in a fatty acid test solution (a reference solution or a test solution) in a condition at a temperature of 25° C., 1 atmosphere, and a relative humidity of 55%, then membranes are formed in sections formed by the plurality of inner frames by bringing the circular frame above a liquid surface, and a time required for at least one formed membrane to be broken is measured;
   Preparation of test solution:
   Reference solution:
   an aqueous solution of iron (II) sulfate heptahydrate is added to the free polyunsaturated fatty acid composition such that an iron concentration is 100 ppm, ethanol is added and homogenized, and then a solvent is removed by using vacuum to prepare a free polyunsaturated fatty acid composition containing 100 ppm of iron in the composition; and 0.5 g of the free polyunsaturated fatty acid-containing composition containing 100 ppm of iron, 0.15 g of 48 wt. % sodium hydroxide, and 9.35 g of purified water are mixed to prepare an aqueous solution containing approximately 5 wt. % of free polyunsaturated fatty acid sodium in the aqueous solution, and the obtained aqueous solution is used as a reference solution;
   Test solution:
   an aqueous solution containing approximately 5 wt. % of free polyunsaturated fatty acid sodium in the aqueous solution is prepared by mixing 0.5 g of the free polyunsaturated fatty acid-containing composition, 0.15 g of 48 wt. % sodium hydroxide, and 9.35 g of purified water, and the obtained aqueous solution is used as a test solution; and
   Preparation of circular frame for test:
   a tool that is formed from plastic and that has five sections divided by inner frames having a thickness of 2 mm in an outer frame having a diameter of 64 mm, an inner diameter of 52 mm, and a thickness of 3 mm is used as the circular frame for test.

5. The free polyunsaturated fatty acid-containing composition of claim 1, wherein a content of the fatty acid alkyl ester is 0.2% or less of the fatty acids in the composition.

* * * * *